US012417539B2

(12) United States Patent
Peters

(10) Patent No.: US 12,417,539 B2
(45) Date of Patent: Sep. 16, 2025

(54) METHOD AND SYSTEM FOR ESTIMATING EARLY PROGRESSION OF DEMENTIA FROM HUMAN HEAD IMAGES

(71) Applicant: COGNES MEDICAL SOLUTIONS AB, Stockholm (SE)

(72) Inventor: Filip Peters, Domsten (SE)

(73) Assignee: COGNES MEDICAL SOLUTIONS AB, Stockholm (SE)

( * ) Notice: Subject to any disclaimer, the term of this patent is extended or adjusted under 35 U.S.C. 154(b) by 332 days.

(21) Appl. No.: 17/920,784

(22) PCT Filed: Apr. 26, 2021

(86) PCT No.: PCT/EP2021/060881
§ 371 (c)(1),
(2) Date: Oct. 22, 2022

(87) PCT Pub. No.: WO2021/214346
PCT Pub. Date: Oct. 28, 2021

(65) Prior Publication Data
US 2023/0162362 A1 May 25, 2023

(30) Foreign Application Priority Data
Apr. 24, 2020 (EP) .................................. 20171315

(51) Int. Cl.
*G06T 7/00* (2017.01)
*A61B 5/00* (2006.01)
(Continued)

(52) U.S. Cl.
CPC .......... *G06T 7/0016* (2013.01); *A61B 5/0077* (2013.01); *A61B 5/372* (2021.01);
(Continued)

(58) Field of Classification Search
CPC ......... G06T 7/0016; G06T 2207/20081; G06T 2207/20084; A61B 5/0077; A61B 5/372;
(Continued)

(56) References Cited

U.S. PATENT DOCUMENTS 10,874,340 B2 * 12/2020 Rau ........................ G16H 20/70
11,049,605 B1 * 6/2021 Peters ..................... G16H 20/70
(Continued)

FOREIGN PATENT DOCUMENTS

KR 102009844 B1 8/2019

OTHER PUBLICATIONS

"International Search Report and Written Opinion," PCT/EP2021/060881, Dec. 7, 2021.
(Continued)

*Primary Examiner* — Wesley J Tucker
(74) *Attorney, Agent, or Firm* — WOMBLE BOND DICKINSON (US) LLP

(57) ABSTRACT

A system for non-invasive estimation of dementia progression. The system includes a computer device and a server. The computer device obtains an image of a subject's head from at least one angle. The server and/or computer device includes a plurality of machine learning models configured to: analyze the image for patterns related to dementia symptoms; and estimate progress of said dementia symptoms of said subject based on the analysis. The server and/or computer device pre-processes the image by performing a plurality of pre-processing steps comprising: importing the image; detecting eyes and shape of the head based on a previously trained machine learning model; rotating the image based on detection of the eyes and shape of the head; normalizing the image to one standard.

17 Claims, 15 Drawing Sheets
(9 of 15 Drawing Sheet(s) Filed in Color)

(51) Int. Cl.
  *A61B 5/372* (2021.01)
  *G06V 10/774* (2022.01)
  *G06V 10/82* (2022.01)
  *G06V 40/16* (2022.01)
  *G16H 50/50* (2018.01)

(52) U.S. Cl.
  CPC .......... *A61B 5/4088* (2013.01); *A61B 5/4842* (2013.01); *A61B 5/7267* (2013.01); *G06V 10/774* (2022.01); *G06V 40/165* (2022.01); *G06V 40/171* (2022.01); *G06V 40/174* (2022.01); *G16H 50/50* (2018.01); *G06T 2207/20081* (2013.01); *G06T 2207/20084* (2013.01); *G06V 10/82* (2022.01); *G06V 40/178* (2022.01)

(58) Field of Classification Search
  CPC ... A61B 5/4088; A61B 5/4842; A61B 5/7267; G06V 10/774; G06V 40/165; G06V 40/171; G06V 40/174; G06V 10/82; G06V 40/178; G16H 50/50; G16H 30/40; G16H 50/20; G16H 50/70
  See application file for complete search history.

(56) References Cited

U.S. PATENT DOCUMENTS

| | | | |
|---|---|---|---|
| 2019/0110754 A1* | 4/2019 | Rao | G06N 7/00 |
| 2020/0214559 A1* | 7/2020 | Krueger | A61B 5/163 |
| 2021/0113139 A1* | 4/2021 | Hiratsuka | A61B 5/742 |
| 2022/0165425 A1* | 5/2022 | Schler | G06N 3/045 |
| 2023/0059768 A1* | 2/2023 | Schler | G06V 10/40 |
| 2023/0162362 A1* | 5/2023 | Peters | G06V 40/165 |
| | | | 382/128 |
| 2023/0222656 A1* | 7/2023 | Wang | G06T 7/0012 |
| | | | 382/128 |
| 2023/0222805 A1* | 7/2023 | Muhsin | G08B 21/043 |
| 2023/0268039 A1* | 8/2023 | Tran | G16H 50/20 |
| | | | 705/3 |
| 2024/0164640 A1* | 5/2024 | Schler | A61B 5/1176 |
| 2025/0006366 A1* | 1/2025 | Cheung | G16H 50/20 |
| 2025/0149179 A1* | 5/2025 | Maeshima | G06V 40/178 |

OTHER PUBLICATIONS

Babak Taati, et al., "Algorithmic Bias in Clinical Populations-Evaluating and Improving Facial Analysis Technology in Older Adults with Dementia," vol. 7, pp. 25527-25534, Feb. 18, 2019.

* cited by examiner

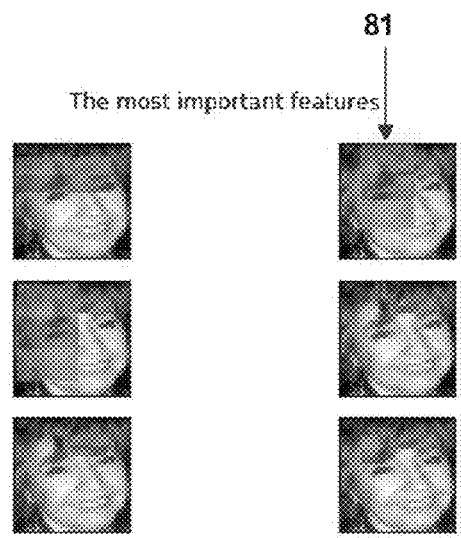
Fig. 8B
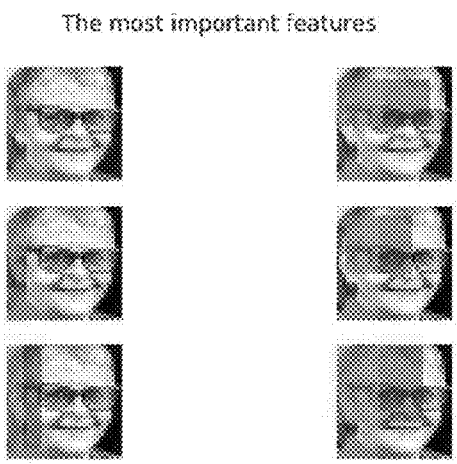
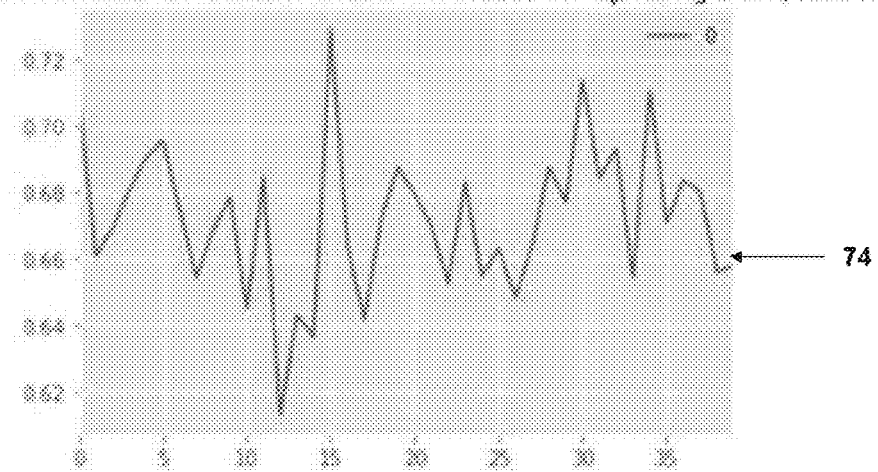
Fig. 8C

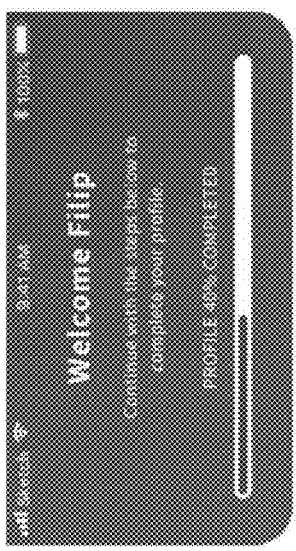
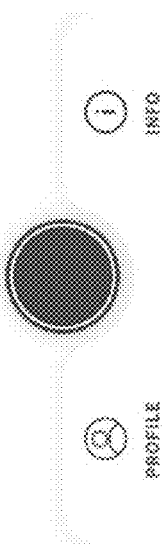
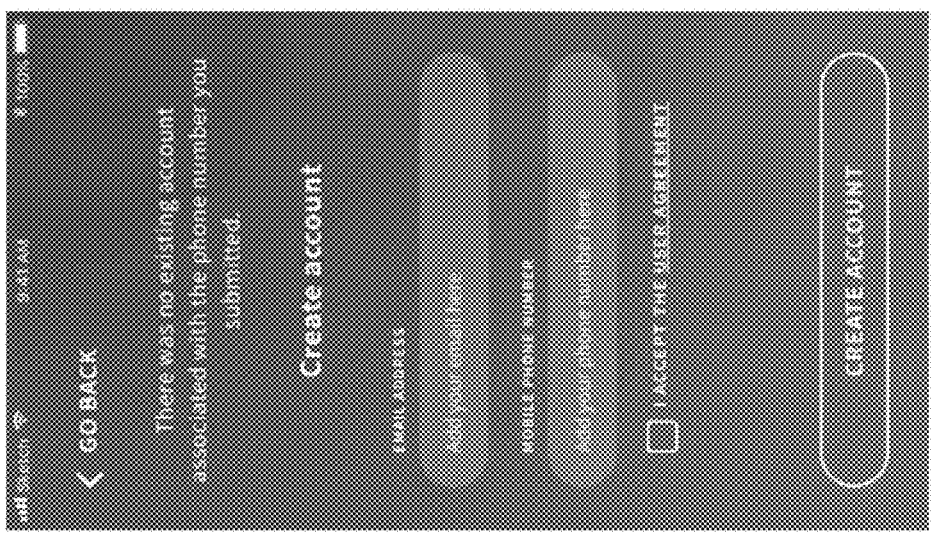
Fig. 10C
Fig. 10B
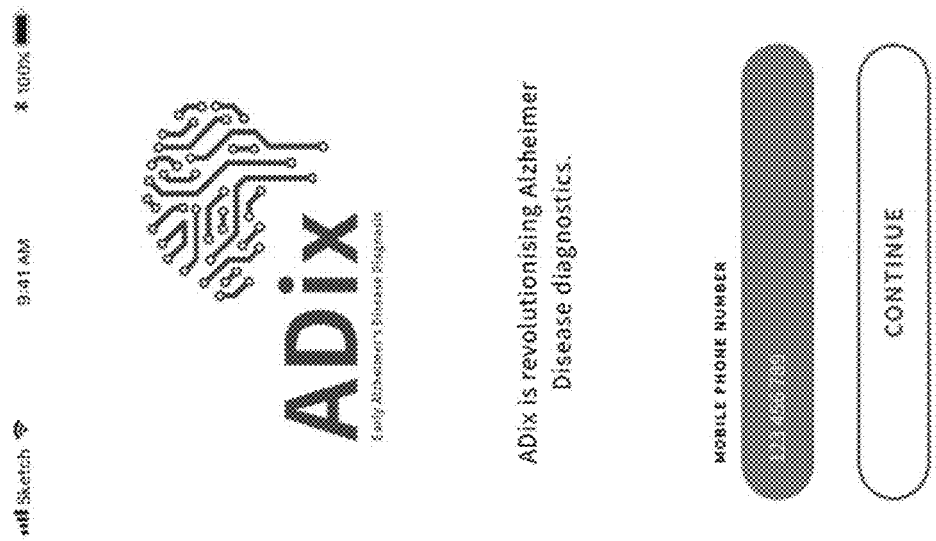
Fig. 10A

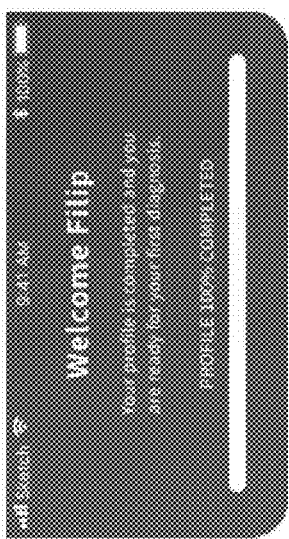
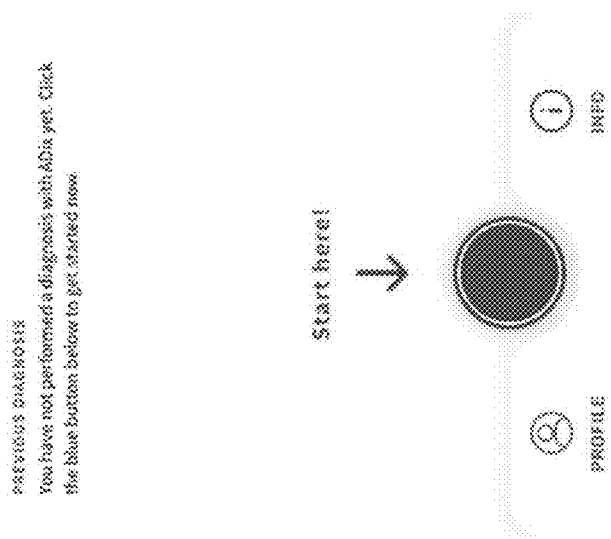
Fig. 10F
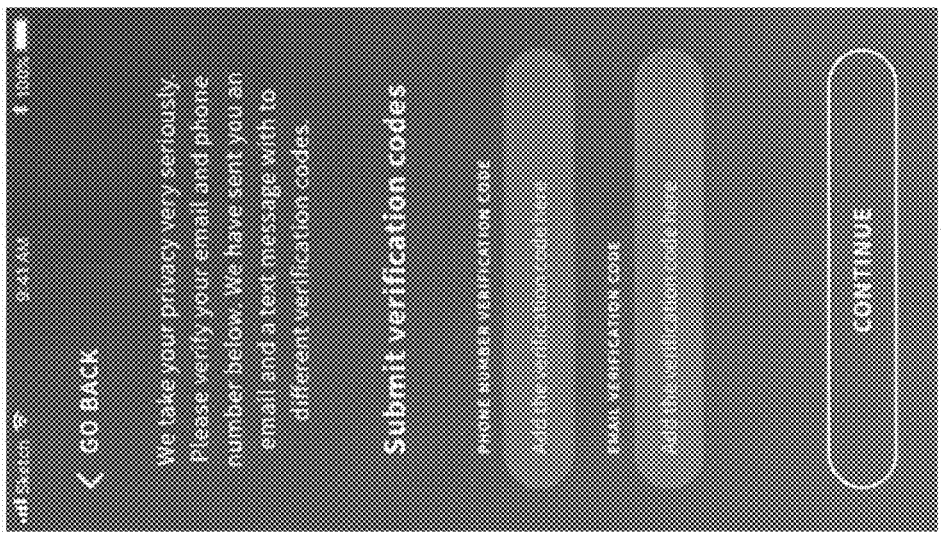
Fig. 10E
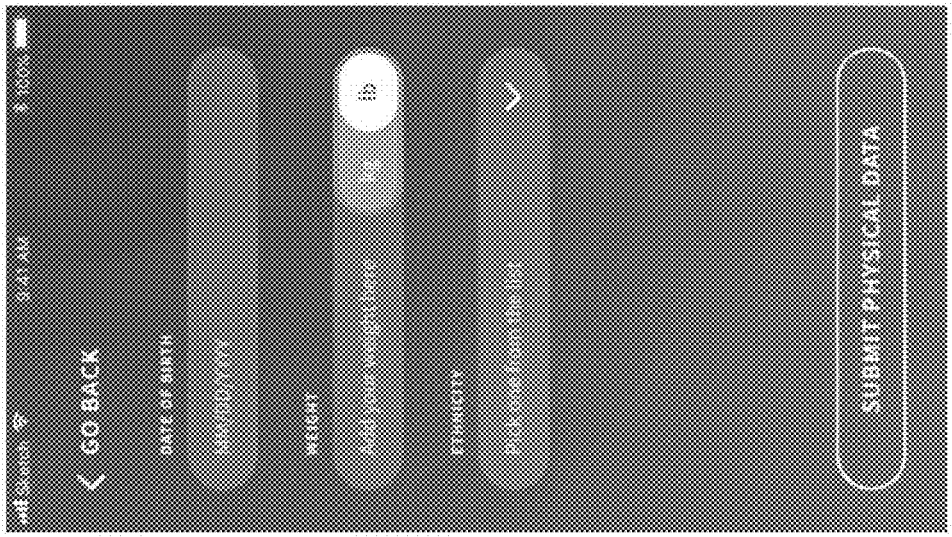
Fig. 10D

METHOD AND SYSTEM FOR ESTIMATING EARLY PROGRESSION OF DEMENTIA FROM HUMAN HEAD IMAGES

CROSS-REFERENCE TO RELATED APPLICATIONS

The embodiments herein claim the priority of the EPO Application filed on April, with the serial number 20171315.3 with the title, "Method and system for estimating early progression of dementia from human head images", and the contents of which are included in entirety as reference herein.

BACKGROUND

Technical Field

This disclosure pertains to estimating the progression of dementia using an image of a subject's head. Especially, the disclosure relates an automated analysis method using machine learning analysis to detect patterns in the image.

Description of the Related Art

Alzheimer disease (AD) is a neurodegenerative disease and type of dementia affecting several million people around the world. As one of the most common forms of dementia, it affects memory, behavior, personality, and cognitive ability. AD risk gradually increases with age. As society grows older, AD prevalence is increasing. It is estimated that AD will double in frequency every 5 years after the age of 65, and the number of individuals in the United States with AD dementia is projected to grow from current 5.5 million to an estimated 14 million by the year 2050. The world's population of AD dementia is projected to increase from 35 million today to approximately 135 million by 2050. It has furthermore been estimated that the average annual societal costs are US$32,865 per person with dementia.

AD is a devastating disease for patients and those around them. Forgetfulness, learning difficulties, and loss of concentration are common symptoms of the disease. As the disease progresses, disorientation, severe memory loss, linguistic difficulties, as well as changes in personality become apparent. There is a tendency for dramatic mood swings such as episodes of anger, expressions of fearfulness, and commonly episodes of apathy and/or depression. General confusion is a common reaction from the patient, especially when encountering new situations, often leading to the person becoming physically disoriented. Mental issues are often accompanied by physical challenges, including odd gait, a decline in coordination skills, inability to properly eat and digest food and drink, as well as an inability to control one's bladder. The gradual progression of the disease sometimes leads to the patient becoming non-communicative, physically helpless, and incontinent. AD is eventually fatal.

The one-off costs of a high-quality dementia diagnosis today are estimated to be around US$5,000 per person. Whilst the net savings of an early diagnosis is around US$10,000 per person with dementia across the disease course, an affordable, accurate, and easy-to-use diagnostic tool for the disease does not exist today. As a consequence, only 20-50% of people with dementia living in high-income countries have received a diagnosis. In low and middle-income countries, the situations remain even bleaker: Fewer than 10% of people living with dementia are diagnosed. In the US, only 16% of seniors receive regular cognitive assessments during routine health check-ups.

Although there is currently no treatment for AD and dementia, science has documented that there are several benefits to the early diagnosis of AD. One study estimates the potential benefits of early AD diagnosis to be as high as $7.9 trillion. There are furthermore benefits from prevention studies that can be harnessed for the benefit of the patients if an early diagnosis can be accomplished. Such studies include the FINGER study, which demonstrated that a multi-domain lifestyle intervention, focusing on managing vascular and lifestyle-related risk factors for dementia and AD, had cognitive benefits for those with a high risk of dementia in the 60-77 years age bracket.

Early AD and dementia diagnosis is important for many reasons. It is important to rule out other conditions which have symptoms that are similar to AD, but which are treatable, as it allows for timely treatment of such conditions. The patient, the patient's family members, and society as a whole also benefit from earlier diagnosis through having the time to more adequately prepare and plan for patients' care. While there is currently no cure available for AD and dementia, medications are available which can alleviate symptoms of AD, such as depression, anxiety, and sleep difficulties. If a treatment is created in the near future, however, like all diseases, the earlier treatment is likely to be most beneficial, reemphasizing the need for an early AD diagnostic tool.

Research has documented that pathological changes arising from AD, typically commences several years before cognitive symptoms become apparent; in some instances, as long as several decades before. Some of these researchers indicate that diagnosis of the disease through the use of biomarkers before symptoms arise, might be a step towards prevention. While prevention and treatment of AD by 2025 has been articulated as a goal of the US government and has been endorsed by other countries, prevention and treatments require the development of new treatments that prevent or delay the onset, slow the progression, or improve the symptoms (cognitive, functional, and behavioral) of AD. Drug development for AD has had a failure rate of 99% in the past decades; similarly, the failure rates for the development of disease-modifying therapies for AD has been 100%. Measurement errors and a lack of specificity during diagnostic evaluations and qualifications of subjects for eligibility for clinical trials can lead to subjects being incapable of responding to treatment due to misdiagnosis, genetics, or specific pathology. Furthermore, difficulty in finding clinical trial participants remains an impediment to developing clinical trials for an AD cure. To make a difference in these fields, diagnosis needs to be made simpler, and more available to make it easier for researchers to develop a treatment.

It is important to note that there is currently no treatment for AD and dementia, something which is likely to have hampered the development of new diagnostic methods. Diagnostic efforts within AD and dementia have hitherto mainly been focused on analyzing the internal properties of the brain. The issue with existing methods of diagnosis are many: Complex neuroimaging techniques such as positron emission tomography (PET) and Magnetic Resonance Imaging (MRI) scans to identify proteins that are thought to cause AD are time-consuming and expensive to perform. Tests focused on identifying changes in cognitive abilities often lack robustness across time as the disease progresses. This is partly because there seems to be an effect of human learning that can make repeated use of such tests unreliable. Cerebrospinal fluid (CSF) biomarkers are another form of diagnostic tool for AD that is being used by clinicians in some countries. Using CSF biomarkers in the diagnostic process of AD is invasive and requires the use of lumbar puncture. The invasive nature of the diagnostic method may cause substantial discomfort to the patient.

Many of the psychological tests that are clinically used to identify AD are to do with deteriorations in memory, particularly in short-term or working memory. Changes to the brain of AD patients typically begin years before cognitive symptoms begin. AD progression needs to be advanced before noticeable memory deterioration can be observed and as a result, these tests lack full capability in diagnosing early-stage AD. There is therefore a need for a simple, non-invasive, and accurate test that can be administered by anyone, anywhere, for detecting early-stage AD before mental deterioration becomes apparent.

With the advent of new technology, new tools for diagnosis have become available to professionals in the field. Three positron emission tomography (PET) radiotracers are currently approved by the U.S. Food and Drug Administration to assist clinicians in the diagnosis of AD, although they cannot yet be used to conclusively diagnose the disease in clinical practice. Today, there is no definitive diagnosis of AD other than going through a postmortem autopsy analysis of the brain. There is furthermore no cure for many types of dementia which has stifled research in the space. Despite being the cause of as many deaths as cancer in the US, it only receives one-tenth of the funding that cancer does.

While it has been previously documented that patients with dementia have impaired recognition of emotions in facial expressions of other people, such symptoms are typically observed in conjunction with the onset of cognitive difficulties. This is often at a stage that is late in the progression of the disease, and therefore not as useful in the early identification of the progression of the disease. Some have claimed that computationally identifying facial features of facial expressions of dementia patients can be used as a tool for dementia diagnosis. Facial expressions of dementia patients can sometimes be experienced as being dull and numb, particularly in the more progressed and later stages of the disease. Several drawbacks characterize the aforementioned approaches. The need for a reactive medium to trigger a facial expression, for example visualizing something that triggers a reaction from the subject, must be uniformly specified and standardized. Similar to the temporal robustness problems of cognitive tests discussed above, it is unclear how stable an approach such as this would be across time and there's a risk of a learning component being present. Similarly, there could be demographic and cultural factors that affect the interpretation of expressions across different populations. In addition, at the point where 'dulled' or 'numbed' facial features pertaining to facial expressions become apparent, the cognitive decline is likely so far progressed that an early diagnosis is unlikely.

The clinical dementia diagnostic process is typically stressful, sometimes involving several invasive procedures, possibly inhibiting people from searching for help. An easy-to-use, accurate and early indication of the progression of AD is of immense importance and is currently lacking in the field of invention today. Such a tool could enable the taking of preventive measures on a multitude of levels, providing immense value to patients, researchers, and society as a whole.

SUMMARY

Accordingly, embodiments of the present disclosure preferably seek to mitigate, alleviate or eliminate one or more deficiencies, disadvantages, or issues in the art, such as the above-identified, singly or in any combination by providing a method, computer program, and a system or noninvasive estimation of dementia progression of a subject.

In an aspect of the disclosure, a method such as a computer-implemented method, for non-invasive estimation of dementia progression. The method may include obtaining at least one image which includes at least a subject's head from at least one angle. The method may also include processing, by a computer device and/or a server, the at least one image by performing a plurality of pre-processing steps; and analysing, by a plurality of machine learning models configured within the server and/or the computer device, features of at least the head from the at least one image for patterns related to dementia symptoms. The method may further include estimating, by the machine learning models, progress of the dementia symptoms of the subject based on the analysis.

In some examples of the disclosure, obtaining at least one image may include capturing the at least one image. Capturing the at least one image may include using a recording device, such as a camera or a computer device with a camera, such as a mobile phone.

In some examples of the disclosure, obtaining at least one image may include receiving, one or more images of the user. The method may further include identifying, a user's head in the one or more images.

In another aspect of the disclosure, a method, such as a computer-implemented method, for non-invasive estimation of dementia progression is described. The method may include capturing at least one image of a subject's head from at least one angle. The method may also include generating at least one dataset from at least one image. Further, the method may include analyzing at least one dataset for patterns related to dementia symptoms. The method could also include estimating the progress of the dementia symptoms of the subject based on the analysis.

In some examples of the disclosure, at least one dataset may be analyzed using a machine learning method trained on datasets comprising dementia-diagnosed subjects.

In some examples of the disclosure, the method may include extracting additional data pertaining to a device on which the method is implemented. The method may further include combining the additional data with at least one dataset generated from at least one image.

In some examples of the disclosure, the method may include detecting lighting and image quality conditions before capturing at least one image and prompting the subject to adjust these.

In some examples of the disclosure, the method may include communicating the estimated progress directly to the subject through a device on which the method is implemented and/or to another device.

In some examples of the disclosure, the method may include offering recommendations pertaining to improving the subject's health conditions.

Collecting data on at least one physical property related to how the computer device on which the method is implemented is held or oriented using a gyroscope and/or accelerometer embedded into the device. This data may be used to approximate whether the user took the photo themselves using the front-facing camera of a computer device, i.e., whether it was a "selfie".

In some examples of the disclosure, the method may include displaying which variables have been most important in determining the progress.

In some examples of the disclosure, the method may include checking whether an input of subject-related information, such as gender and age, has been correctly entered.

In some examples of the disclosure, the check may be performed by analyzing the image and ensuring that entered data corresponds to that indicated in the image, e.g., gender and/or age. In some examples of the disclosure, the check may be performed by identifying abnormally large numbers that have been entered.

In some examples of the disclosure, the method may include estimating cerebral blood flow.

In some examples of the disclosure, the method may include estimating the risk of Parkinson's disease progression.

In some examples of the disclosure, the method may include visualizing estimated internal properties of the subject's brain.

In some examples of the disclosure, the method may include estimating the likelihood of proteins, such as Amyloid Beta or Tau, being present in the subject's brain.

In some examples of the disclosure, the method may include combining the dataset with data obtained using a sensor, such as data collected from an infrared sensor and/or echocardiographic devices.

In a further aspect of the disclosure, a computer program including instructions which, when the program is executed by a computer, cause the computer to carry out the method described above is disclosed.

In another aspect of the disclosure, a system that includes a processor or means configured to perform the above-described method is disclosed. The system may include a single device for performing all the steps by may also be a system of devices where each device is implemented to perform a particular part of the described method. For example, a first device used by the subject or a practitioner treating/diagnosing the subject for collecting the information. The information is sent from the first device to a server configured for processing the collected information and to send the result to either the subject or a practitioner treating/diagnosing the subject.

In yet another aspect of the disclosure, a computer-implemented machine learning method for non-invasive estimation of dementia progression is described. The method may be trained to detect patterns related to dementia symptoms in at least one dataset generated based on images of a subject's head.

A system for non-invasive estimation of dementia progression. The system includes a computer device and a server. The computer device captures at least one image of a subject's head from at least one angle. The server and/or computer device generates at least one dataset from the image received from the computer device over a network. The network may be a wired or a wireless network, and the examples may include but are not limited to the Internet, Wireless Local Area Network (WLAN), Wi-Fi, Long Term Evolution (LTE), Worldwide Interoperability for Microwave Access (WiMAX), and General Packet Radio Service (GPRS). The server and/or computer device includes a plurality of machine learning models configured to: analyze the dataset for patterns related to dementia symptoms; and estimate progress of the dementia symptoms of the subject based on the analysis. The server and/or computer device pre-processes the dataset by performing a plurality of pre-processing steps comprising: importing the image; detecting eyes and shape of the head based on a previously trained machine learning model; rotating the image based on detection of the eyes and shape of the head; normalizing the image to one standard; and estimating the age of the subject based on a previously trained machine learning model.

In an aspect, the dataset is analyzed using the machine learning models trained on datasets comprising dementia-diagnosed subjects.

In an aspect, the computer device is configured to detect lighting quality conditions and image quality conditions before capturing the image and prompting the subject to adjust the lighting quality condition and image quality condition.

In an aspect, the server and/or computer device is configured to communicate the progress estimated by the machine learning models to the subject; and offer recommendations pertaining to improving the health conditions of the subject.

In an aspect, the computer device includes a gyroscope and an accelerometer to detect the orientation of the computer device.

In an aspect, the computer device is configured to display one or more variables that are determining the progress of the dementia symptoms.

In an aspect, the server and/or computer device is configured to check whether an input of subject-related information has been correctly entered.

In an aspect, the server and/or computer device is configured to estimate cerebral blood flow.

In an aspect, the server and/or computer device is configured to estimate the risk of Parkinson's disease progression.

In an aspect, the computer device is configured to: visualize estimated internal properties of the subject's brain.

In an aspect, the computer device is configured to estimate a likelihood of proteins being present in the subject's brain.

In an aspect, the computer device includes an infrared sensor and an echocardiographic device to obtain data from non-invasive measurement of the user's brain, wherein the data obtained through the infrared sensor and the echocardiographic device is combined with the dataset of the image before machine learning analysis.

BRIEF DESCRIPTION OF THE DRAWINGS

The present invention is illustrated by way of example and not limitation in the figures of the accompanying drawings in which like references indicate similar elements. The patent or application file contains at least one drawing executed in color. Copies of this patent or patent application publication with color drawing(s) will be provided by the Office upon request and payment of the necessary fee.

FIG. 8A, FIG. 8B and FIG. 8C illustrate data pertaining to an experimental study;

DETAILED DESCRIPTION OF THE EXAMPLES HEREIN

Figure 1:
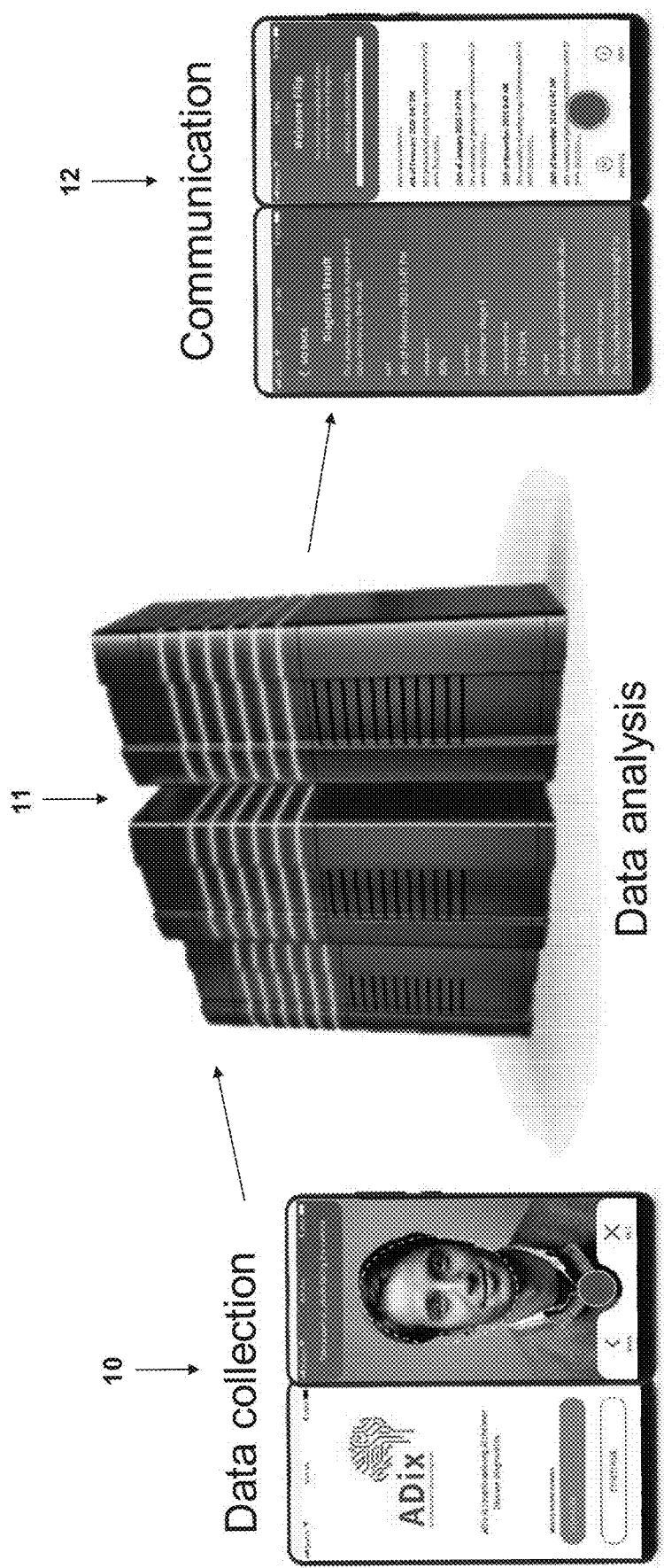
FIG. 1 illustrates a schematic overview of a process according to the description.

Specific examples of the disclosure will now be described with reference to the accompanying drawings. This disclosure may, however, be embodied in many different forms and should not be construed as limited to the examples set forth herein; rather, these examples are provided so that this disclosure will be thorough and complete, and will fully convey the scope of the disclosure to those skilled in the art.

The following disclosure focuses on examples of the present disclosure applicable to estimate the early progression of dementia from human head images. The description covers a method that may be implemented on a computer. The method may also be implemented as a computer program or a device.

A computer may here be any type of data processing device. The data processing device may be implemented by special-purpose software (or firmware) run on one or more general-purpose or special-purpose computer devices. In this context, it is to be understood that each "element" or "means" of such a computer device refers to a conceptual equivalent of a method step; there is not always a one-to-one correspondence between elements/means and particular pieces of hardware or software routines. One piece of hardware sometimes comprises different means/elements. For example, a processing unit serves as one element/means when executing one instruction, but serves as another element/means when executing another instruction. In addition, one element/means may be implemented by one instruction in some cases, but by a plurality of instructions in some other cases. Such a software-controlled computer device may include one or more processing units, e.g., a CPU ("Central Processing Unit"), a DSP ("Digital Signal Processor"), an ASIC ("Application-Specific Integrated Circuit"), discrete analog and/or digital components, or some other programmable logical device, such as an FPGA ("Field Programmable Gate Array").

The data processing device may further include a system memory and a system bus that couples various system components including the system memory to the processing unit. The system bus may be any of several types of bus structures including a memory bus or memory controller, a peripheral bus, and a local bus using any of a variety of bus architectures. The system memory may include computer storage media in the form of volatile and/or non-volatile memory such as read-only memory (ROM), random access memory (RAM), and flash memory. The special-purpose software may be stored in the system memory, or on other removable/non-removable volatile/non-volatile computer storage media which is included in or accessible to the computer device, such as magnetic media, optical media, flash memory cards, digital tape, solid state RAM, solid state ROM, etc. The data processing device may include one or more communication interfaces, such as a serial interface, a parallel interface, a USB interface, a wireless interface, a network adapter, etc., as well as one or more data acquisition devices, such as an A/D converter. The special-purpose software may be provided to the computer or data processing device on any suitable computer-readable medium, including a recording medium and a read-only memory.

An example may here be a handheld device, such as a smartphone. In some examples may the method be implemented to run on a single computer. Additionally, and/or alternatively, in some example, may part of the method be implemented to run on a computer used by a subject to be tested and other parts of the method may be implemented to run on at least one server.

In an example, the images to be analyzed may be sourced from a pre-existing data repository of images. Analysis based on pre-existing data repositories have the benefit of offering a retrospective analysis, where there can consequently be no conscious or unconscious effort from the user to impact the result of any results, that could bias the validity of the results.

Examples of such data repositories may include but is not limited to social media sites such as Instagram, Facebook, Pinterest, etc. These data repositories may comprise of a function to identify individuals within a particular image, allowing for determination of dementia risk assessment based on a temporal analysis and/or analysis of the environments where the images were taken and/or analysis of objects, artefacts and people present within the image. Some artefacts may indicate lifestyle choices known to be associated with increased risks of dementia, such as alcohol consumption and/or diet. Data repositories may also include computer systems that are able to segment images and identify different individuals within the image. An example of such data repositories may be any variation of "smart albums", including but not limited to digital image albums that are able to identify persons and sort according to these albums, commonly found in iOS and Android based smartphones. Such computer systems may be further based on operating systems that comprise Amazon Fire®, One UI®, Librem®, EMUI®, Android®, and iOS®. Such data repositories may furthermore be cloud based or may be run in a smartphone application, e.g., google photos. In an example, a temporal analysis of such data repositories may be performed to determine dementia risk.

In one embodiment, changes in facial features and areas of a person between different images and/or across time, may provide insight into the dementia risk of that person and/or how quickly a dementia risk factor may be progressing. A temporal analysis of the user's images may further be performed by comparing a plurality of areas of a user's face based on a recent set of one or more images with a plurality of areas of a user's face in an older set of one or more images, and using differences between these sets to estimate dementia progression. The areas chosen for comparison may be chosen at random. Atrophy in one part of the brain may for example cause an internal brain shrinkage which causes a shrinkage to the outside of the head. This may lead the outside of the head to reflect light at a new angle, something that can be detected in an image through differences in the amount of pixels that can be observed. The comparison of different regions of the image across time, allows for the identification of image commonalities across different light conditions, and therefore better control of external light factors which may change the reflection between different images. Changes in these image commonalities may further indicate changes to the brain which may be related to the progression of dementia.

In an example, differences between the right and left regions of the human image head may indicate dementia progression resulting from semantic dementia, which is predominantly associated with temporal lobe atrophy, where the left atrophy is greater than the right. Further, certain proteins in the brain, e.g., Tau and TDP43A, may demonstrate similar brain atrophy patterns in one area of the brain, such as frontotemporal volume loss, but may be less extensive on the right in groups of patients that belong to a certain Tau group, such as 4-repeat-tau group. A further example of these differences is that there may be greater parietal involvement in patient groups such as TDP43A. TDP43C patient groups further demonstrate greater left anterior-temporal involvement. These differences in atrophy of different parts of the brain can be many and are to a large extent unexplored. It is the identification of these differences in atrophy of different regions of the brain which is reflected on the outside of the head which may offer important clues to estimating the progression of dementia.

Further, it is well-known that Magnetic Resonance Imaging (MRI) can identify sulci widening and narrowing gyri (Cai et al., 2017) as well as neuroinflammation (Quarantelli (2015). These are both developments known to be correlated with dementia. It is furthermore known that faces can be reconstructed from MRI images using image-based machine learning methods (Schwarz et al, 2019). It is therefore plausible that reversing the process, whereby image-based machine learning methods can be used to reconstruct MRI images, can lead to insights into changes in the brain. The step involving reconstructing the MRI images, is likely not crucial to arriving at important insights about changes to the internal structure of the brain that may be related to dementia. Therefore, if machine learning can be used to reconstruct faces from MRI images, and if MRI can detect features of early dementia as is well-known, then exterior features of the head may hold observable information of dementia developments within the brain, normally only visible through MRI.

In an example, an emotion recognition model may be applied to a data repository comprising images of the user to determine the trend of the user's emotions over time. An emotion recognition model may be trained using common facial expressions related to emotions, e.g., a smile being associated with happiness, frowns with discontent, tears with sadness, etc. A trend analysis of emotions may take the form of but is not limited to analysing the number of emotions identified, the types of emotions identified and/or the strength of the emotions that have been identified. Emotional deficit is related to dementia, and by analysing the prevalence of emotions across more than one image over time, one may be able to elicit a trend in the progression of dementia.

In an example, an indication of whether the image was taken using the front or back camera of a user's computer device may further indicate that the user took the photo of themselves.

In an example, metadata of an image pertaining to the user may further be analyzed to identify variables of interest. E.g., certain variables, such as geographical location of where the image was taken may be related to a likelihood of the person in the image being associated with a geographical area where prevalence of dementia may be higher. Further, metadata pertaining to time the image was taken may furthermore provide helpful insights into nocturnal and/or sleeping habits of the subject, factors well-known to be correlated with dementia rates. Metadata may further comprise of information about the camera was used to take the image, e.g., if it was a forward or back-camera, technical specifications of the camera used, etc.

In an example, the neuroactivity of the user may further be analyzed using an electroencephalography (EEG) device. Neuroactivity is known to be correlated with dementia and could further help differentiate non-dementia from dementia subjects to estimate a progression of dementia.

What is hereby presented are devices, systems, and methods to enable the estimation of progression of dementia through automated machine learning methods of one or more images of a human head. The following methods, devices, and systems may improve the way we diagnose, treat, and research dementia in one or more ways. These benefits may include but are not limited to helping individuals identify early dementia progression, enabling easy and widespread use of dementia progression estimation, thereby reaching more people and at a substantially lower cost. Reducing the stress associated with some diagnostic modalities within the medical field through an easy-to-use, affordable and accurate at-home test could substantially help reduce the number of dementia patients that fail to be identified in the early stages of the disease.

Presented herein, is the first documented study on AD and dementia patients that demonstrates the potential to accurately diagnose the disease based on an analysis of the external features of the head, using machine learning.

Machine learning methods presented herein are specifically adapted to detect changes in the microstructure and shape of the head. AD is thought to be caused by the build-up of proteins inside the head and the medical field has been primarily focusing on studying internal brain properties, whether it be internal imaging of the brain or analyzing fluids from the body. The idea that AD can cause changes to the external physical properties of the head that are visible and detectable by machine learning-based technology has hitherto not been documented. These changes are small and difficult to detect with the human eye which has likely been a contributing factor as to why it has been overlooked by previous researchers.

There are several ways that this disclosure and the examples herein may help improve dementia-related diagnostic methods:

Affordability as a broad-based screening tool. The cost of dementia diagnosis today is often too high to motivate a broad screening process across populations that are at risk of developing the disease. For example, PET scans, which are just one step in the diagnostic process, cost several thousand U.S. dollars and are therefore difficult to apply as a widespread early screening tool.

Easy access for all patients. Today, easy access to dementia clinics and expertise is not always readily available. An important role that this disclosure and the examples herein may play is the affordable application of early diagnosis in both less developed countries where as many as 90% of dementia patients go undiagnosed but also helping fill the gap of as many as 80% in high-income countries who fail to get a timely diagnosis.

Avoiding stressful diagnostic methods (PET scans, MRI scans, CSF spinal samples including lumbar puncture, etc.). With less stress involved in the diagnostic process, this could increase the willingness of potential patients to search for helping themselves.

Early diagnosis, before cognitive symptoms, affects the person. Cognitive tests that indicate symptoms of cognitive decline often reflect symptoms that occur long after the physical onset of the disease which typically happens 20 years before cognitive symptoms become apparent.

Robustness across time. Because the test involves observing the external physical manifestations of the head there is no inherent bias from the subject being observed. This is in contrast to many cognitive tests where there is often a learning component over time as well as difficulties in interpretation differences resulting from demographic, cultural, and lingual factors.

That changes to the internal structure of the head resulting from dementia may translate into external physical changes to the head, has hitherto been unknown because such changes are not readily visible to the human eye. A common feature of dementia patients' brains is that they lose between 200-300 grams of weight throughout the course of the disease; this brain atrophy for AD patients is significantly higher than populations of similar age.

This constitutes a substantial part of the average brain which only weighs around 1198 grams for women and 1336 grams for men. It is furthermore known that physical manifestations to the brain resulting from dementia begin 20 years before behavioral and cognitive symptoms become apparent.

The use of machine learning methods, including but not limited to the use of image analysis including decision tree-based machine learning methods, artificial neural networks, and convolutional neural networks, can provide insights into the likelihood and advancement of AD and dementia-related symptoms. The systems and methods presented herein could furthermore provide new insights into the research of AD and how the physical manifestations of the disease take place and progress, thereby deepening the understanding of the medical field. The ability for the invention to be widespread and affordable to use will allow for a deeper understanding of how geographic components affect the disease to be explored.

The method presented may offer an affordable way of diagnosing AD and dementia today. This may offer earlier and more widespread understanding to patients all around the world who are unable to receive a clinical opinion on the progression of the disease because of lack of access and/or current prognostic tests being too expensive to carry out on a large scale. It can furthermore help speed up clinical trial recruitment and could therefore help reduce costs of developing a cure for AD. To alleviate patient screening for clinical studies within the research of new drugs and treatments for dementia-related diseases is of great importance because today, as many as 80 percent of recruited individuals fail to meet inclusion criteria.

Dementia affects different parts of the brain at different times, and one way of increasing the accuracy of estimating the progression of the disease is by analyzing images of different sides of the head. Such an analysis of the entire head is one way of increasing the chances of a machine learning model to estimate progression with a high degree of accuracy. In some examples of the disclosure, the additional use of patient-specific data, including but not limited to age, gender, weight, height, can be used to further enhance the diagnostic accuracy of the analysis.

For example, both age and gender are related to the high prevalence of AD and dementia. Socioeconomic status (SES) is also a risk factor related to AD and dementia, with lower SES and education levels indicating a higher risk of AD and dementia. It has furthermore previously been documented that socioeconomic status is related to smartphone usage. One example is that among low socioeconomic status smartphone users, a large number of applications are typically uninstalled, and lower SES groups spend more money on applications and install more applications overall. It is therefore not unlikely that it follows that user/usage data that may be derived from a smartphone, is likely to be correlated to AD and dementia risk factors, which may help estimate the progression of such diseases. Combining such data with the datasets generated from the image data could improve the overall accuracy of a diagnostic process.

Another potential use of smartphone data to estimate the progression of dementia is the use of the gyroscope and/or accelerometer data that many computer devices with communication abilities come equipped with today. Patient tremors have been identified as indicative of dementia progression in at least one previous study, showing that motor signs increased as the disease progressed. Such motor signs could very well be identified through the use of a gyroscope within a smartphone while the subject is using the application. Additional studies suggest that remaining socially and mentally active throughout life may support brain health and possibly reduce the risk of AD and other types of dementia. Remaining socially and mentally active may help build cognitive reserve. It has previously been shown that cell phone usage has had an effect on neuronal changes and social engagement. This could in turn have a significant effect on the progression of dementia. The ability of modern mobile electronic devices, in particular smartphones, to provide useful data collection and data creation tools may be insightful in its application to neurodegenerative diseases such as dementia. The data collected from smartphones may provide useful data information on the smartphone use of its users that could, in turn, provide useful indications of the user being at risk to a number of different neurological diseases.

An aspect of including smartphone data in the data analysis is that the data has the potential to measure behavior continuously, without being affected by the patient's awareness of the data collection process which might alter their behavior. Examples of such devices could be but are not limited to, handheld electronic mobile data transmission devices operating on Apple's iOS operating system, Google's Android operating system, BlackBerry's operating system, and or Huawei's operating systems.

Standardizing the digital images that feed into the neural networks may be of great importance and data scientists typically spend a large amount of time preparing and pre-processing data. Real-world data may be messy and often needs to be normalized, transformed, have outliers removed, or otherwise processed so that its characteristics can help the model produce quality results. Challenges that typically arise in this process are partly minimized by executing the data collection part of this process through a smartphone application. The smartphone application guides the user to take photos from certain, pre-specified angles and lighting conditions to standardize the quality of the digital images and remove the risk of noisy data interfering with the ability of machine learning to uncover meaningful patterns in the datasets.

Decreased cerebral blood flow (CBF) is another known symptom of AD with lower cerebral blood flow being associated with dementia. CBF has been shown to be observable using optical methods such as photoplethysmography. It is therefore likely that external features associated with CBF may be detectable using machine learning based image analysis. CBF may be identified in an image of a human head by looking at patterns and/or changes in skin colour and skin composition which may result from changes in cerebral blood flow.

In one example of the disclosure, the generated dataset may be combined with an infrared camera, a photoplethysmographic sensor and/or a heat-detection camera to detect changes arising in the temperature of the skin of the head resulting from changes in CBF.

While focused ultrasound therapy has been used to open the blood-brain barrier in the brain to allow for new treatment approaches in the dementia research space, ultrasound for the purpose of diagnosis for the progression of dementia has been limited. Given the documented changes to the exterior of the brain that have been revealed in this document as well as the known brain volume and structure changes to persons with dementia, it is likely that by combining machine learning methods with ultrasound technology applied to the brain region may be of diagnostic value. In one example of the disclosure, the original dataset uncovered from the head images may be combined with ultrasound imaging to yield final results. In such a way, one can combine external head information with internal, brain information, thereby providing a more holistic overview of the brain.

In some examples of the disclosure, the variable importance may be visualized and communicated to the user or another party of the user's choice, such as but not limited to, a clinician or hospital. This could be helpful for a clinician in helping determine other diagnostic steps that could be helpful for the person to carry out. In another example of the disclosure, an estimated visualization based on imaging techniques of the internal properties of the head or brain such as PET-scans, MRI scans, or similar techniques, could provide additional information of the inner working of the brain. Such visualization techniques could also help further the AD and dementia research community's understanding of the progression of the disease, perhaps at a reduced need for expensive internal brain imaging modalities. Well-established machine learning methods such as Generative Adversarial Networks (GANs) have been well documented in their ability to create synthetic imagery outputs based on trained data. A machine learning model may be trained to generate one or more visualizations of the internal properties of a brain of a user using MRI-images corresponding to that same user as training data. The choice of machine learning algorithm and parameters thereof may be chosen by simultaneously fitting a machine learning model to each individual dataset of image data pertaining to each user, storing the r-squared of each iteration and testing a new machine learning configuration for each subsequent iteration. The machine learning configuration with the highest global optimum (based on a summary metric such as but not limited to mean and/or median r-squared) would be chosen. The final model could then be used to transform any human head image into visualizations of internal properties of the same user. Unbalanced datasets may be controlled for by reducing the desired pixel size of each image in the independent variable dataset (ie. MRI-image dataset).

Machine learning models used for multi-dimensional outputs, such as convolutional neural networks may be used. In another embodiment, building a machine learning system to generate images of the internal properties of the brain based on MRI-image training data may comprise the following steps:
1. Training a discriminative machine learning model
2. Training a generative machine learning model
3. Generating one or more visualizations of the internal properties of the brain
4. Using the discriminative model to estimate the quality of the generated visualizations
5. In a reiterative process, the generative model would learn from feedback from a discriminative model and optimize its generated data to "beat" the generative model.

Brief Presentation of Results from an Experimental Study

In a pilot study that was completed in February of 2020, the images of heads of 1329 persons were analyzed using a number of different machine learning methods to predict AD. As previously mentioned, the only way to diagnose AD and dementia today is through a post-mortem autopsy of the brain. The average age of death for the two groups was approximately 73. Using the Deep Expectation database of more than 500 k+ people, the average age at the time that each photo was taken in the sample set, was estimated to have been 48 with a standard deviation of 9 years. On average, the photos were taken approximately 25 years before the subjects' death. Despite having a comparatively young cohort by clinical AD and dementia diagnostic standards, sensitivity and specificity look very promising: The results of the study include the sensitivity of 66%, a specificity of 72%, and overall accuracy of 71%.

In total, facial images of 1329 separate people were used. 217 (16.3%) of these had dementia and 1112 did not. The dataset consists of 686 men and 643 women in total. 138 of those with dementia were women (21.5% of total women), and 79 (11.5% of total men) were men. This reflects the lifetime risk of getting AD for each gender post 65 years of age. Subjects without AD were split approximately evenly. The dataset was split into a 75% in-sample training dataset and a 25% out-of-sample testing dataset. Pictures were scraped online by three different people to avoid data collection/image editing bias. The accuracy of diagnosis in the non-AD dataset was checked by a 4th person to remove overlapping diagnoses. A number of different machine learning methods were tried and combined in a variety of ways. 100+ of Convolutional Neural Networks were trained and stacked to yield our final results. The previously existing cv2. CascadeClassifier was used to standardize the pictures by identifying the location of the eyes and the shape of the face.

Figure 8A:
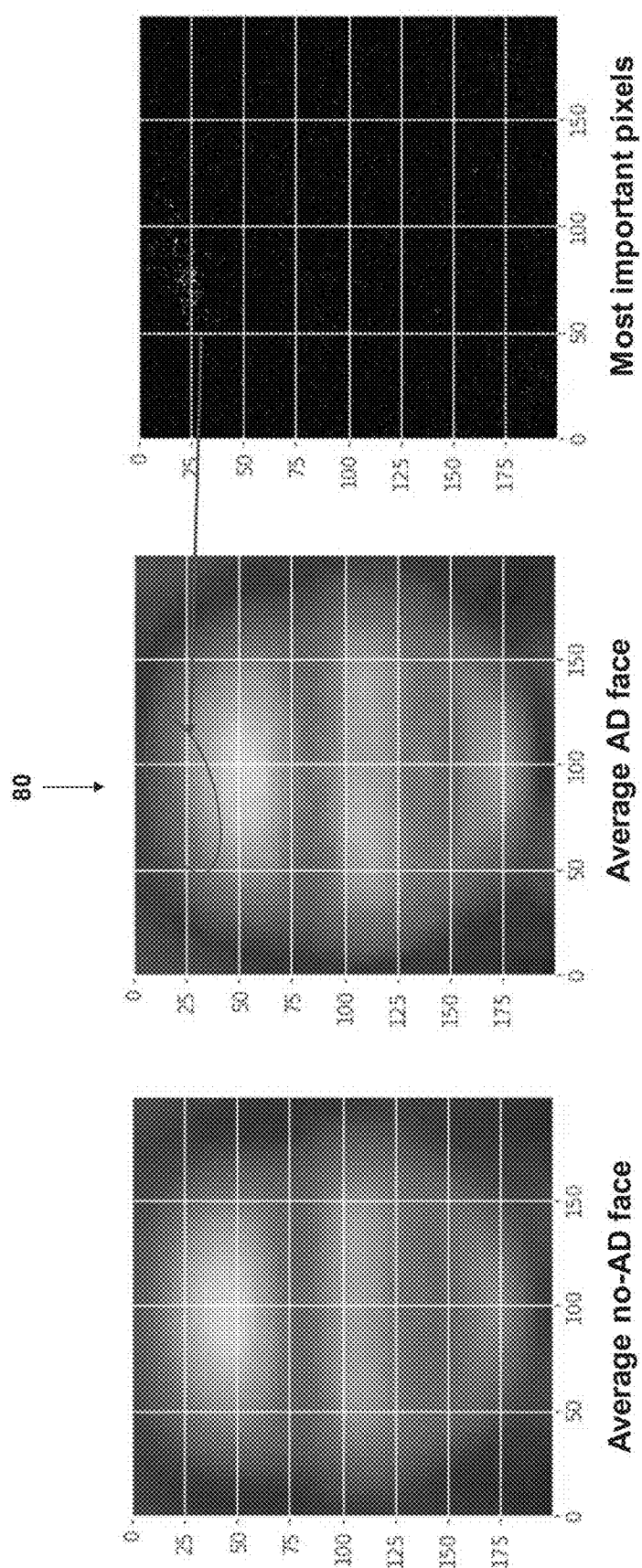

To ensure robustness, 40 different random states were tried in terms of selecting a training and testing dataset. This can be seen in FIG. 8C. The mean macro recall score (average of sensitivity and specificity) across all random states was 66%. We chose a random state which reflected this mean 74 so that there was no bias in our data from our initial generation of training and testing datasets. In one use of the Random Forest Classification algorithm, 20 feature importances were extracted to give an idea of which pixels are on average the most important in determining the final prediction of the model 80. This is illustrated in FIG. 8A and FIG. 8B. A second type of machine learning method, employing a well-known and standard image recognition technique known as Haar-feature-based cascade classifiers, is represented by FIG. 8B. What is interesting to note, and which lends support to the conclusions drawn from the study, is that both ways of looking at feature importances arrived at similar conclusions about what areas 30 of the head 80, 81 are most important in driving final results.

Based on previous academic work in the machine learning and artificial intelligence literature, it is likely that a +90% sensitivity and +90% specificity in a clinical trial with a larger dataset and higher quality data can be achieved. Several image classification studies in the machine learning literature indicate that such improvements from increased sample size and better quality pictures can be attained. Increasing the sample size from the current 1.2 k images to 4 k+ images could increase accuracy by 40%. Using images from multiple angles could furthermore improve accuracy by 10%. Higher quality and more standardization (i.e., that images are taken with a similar angle, similar color, similar lighting conditions, and similar general environment conditions images) would likely also boost accuracy. Accuracy is likely to increase with a slightly older patient cohort as this means that physical symptoms become more progressed and likely more visible. For example, plaque build-ups inside the brain, such as amyloid-beta, are known to increase from the age of 50. Additional and more accurate data about the user, including but not limited to age, gender, demographic and socioeconomic data, when combined with the physical manifestations are likely to yield improved accuracies.

Specific examples of the disclosure may be described with reference to the accompanying drawings. The described examples may, however, be embodied in many different forms and should not be construed as limited to the examples set forth herein; rather, these examples are provided so that this disclosure will be thorough and complete, and will fully convey the scope of the disclosure to those skilled in the art. The terminology used in the detailed description of the embodiments illustrated in the accompanying drawings is not intended to be limiting of the disclosures. In the drawings, like numbers refer to like elements.

The following description focuses on examples of the present disclosure that applies to the diagnosis of dementia and in particular to Alzheimer disease. However, it will be appreciated that the invention is not limited to this application but may be applied to many other neurodegenerative diseases, including, for example, Parkinson's disease (PD) and PD-related disorders, Prion disease, Motor neuron diseases (MND), Huntington's disease (HD), Spinocerebellar ataxia (SCA) and Spinal muscular atrophy (SMA).

To ensure brevity, references to specific machine learning methods such as cross-validation techniques or references to specific machine learning algorithms such as Random Forest Classifiers, are considered general knowledge and are well-known to somebody in the field. It is furthermore thoroughly covered in many introductions to machine learning books.

Figure 4:
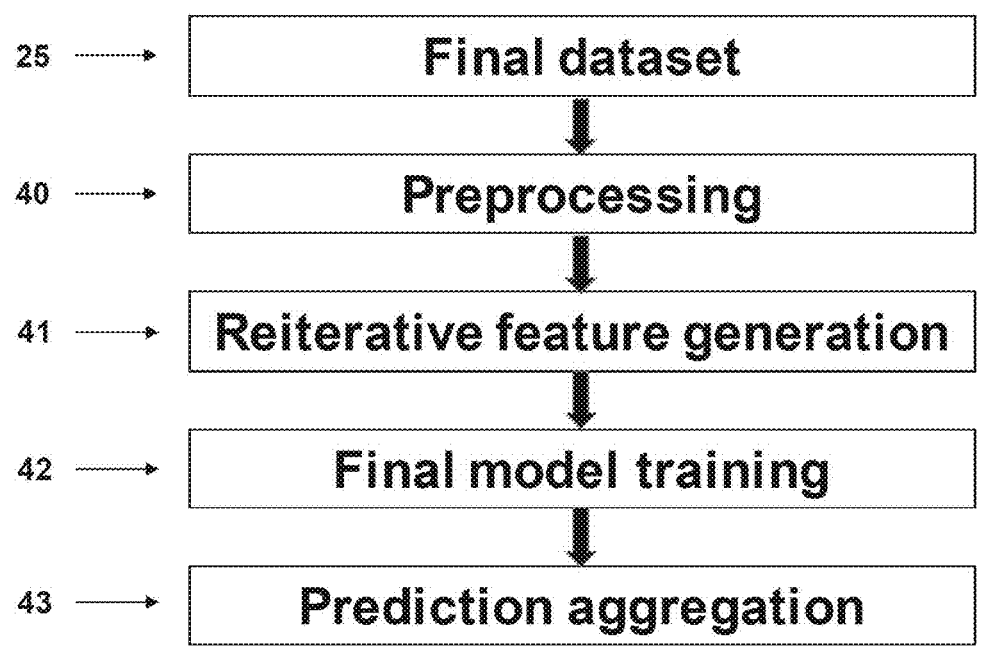
FIG. 4 illustrates an example of a machine learning method that may be applied in the process.

The broadest definition of the disclosure may be observed in FIG. 1. First, a data collection step is performed 10. The data collection may be done using a handset that comprises a camera, such as a mobile phone. The data collection may also be done using a computer and a photo may be downloaded from a camera or a camera connected to the computer, such as a webcam. The collected data may be uploaded to a server 11 and analyzed using a plurality of machine learning models, for example, as illustrated in FIG. 4 on the server, on the computer device, or another computer device. Results from the automated machine learning-based data analysis may then be executed through communication step 12 to the user and/or another recipient.

Figure 2:
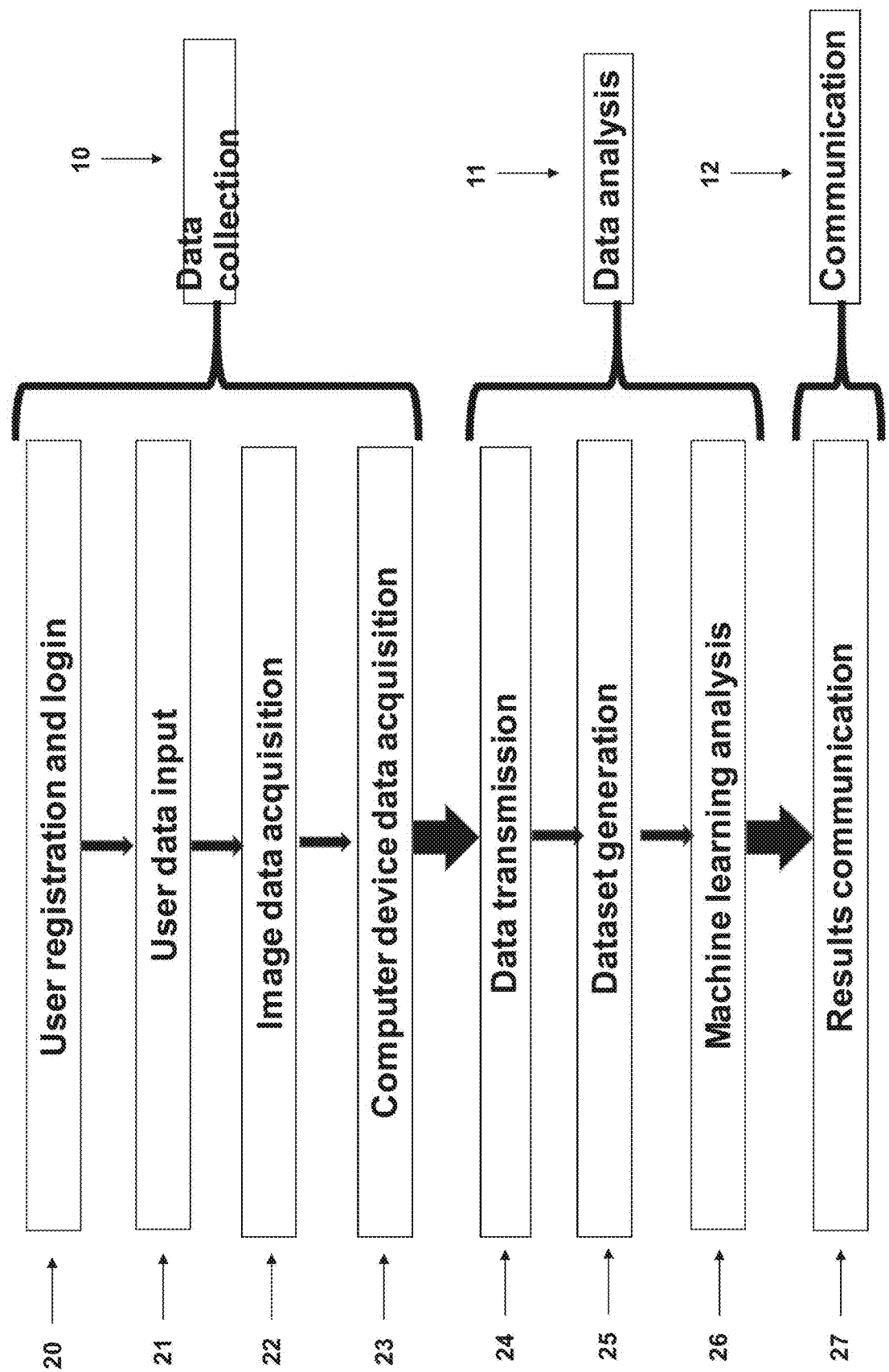
FIG. 2 illustrates a more in-depth schematic overview of the entire process.

FIG. 2 presents a more detailed process overview. The data collection process begins with user registration and login process 20 that may entail a verification process through a personal ID in the form of a passport, another form of national ID, or another form of officially accepted means of identification. A user agreement covering aspects such as data sharing, privacy, and user rights may be presented and required to be agreed to by the user or otherwise authorised party. The application may furthermore be prompting for contact information from the user and/or prompting the user for contact information pertaining to a clinician of the user's choice and/or contact information pertaining to an emergency contact of the user.

The user may then be prompted to fill out information pertaining to the user 21. This data may include but is not limited to age, ethnicity, country of residence, country of birth, eye color, weight, height, etc. In one example of the application, the entered data is verified by our algorithm that it has been accurately entered. For example, using image recognition techniques from the machine learning literature, one may estimate if the gender, age, and height that is presented within the personal ID documents that have been submitted, matches the user data input. If a discrepancy is found, this may be communicated to relevant parties and the user could be notified in order to re-enter such data.

The data collection process is furthermore characterized by that one or more images of the user's head are taken by the user using a computer device 22, such as a smartphone or a camera connected to a computer, etc. In one embodiment of the disclosure, the user is prompted to take one or more photos from different angles of the user's head. The user can be prompted to ensure that the photos are not blurry, that there are no objects covering the user's face, and that the lighting and quality meet sufficient standards. Computer device data may also be acquired at this point 23. Such data may comprise information such as usage statistics, data relating to information collected from a gyroscope or accelerometer, temperature, infrared sensor, microphone, electrocardiographic sensors, photoplethysmography sensors, echocardiographic technologies, or any sensor within a similar category of non-invasive clinical measurement techniques.

Figure 10I:
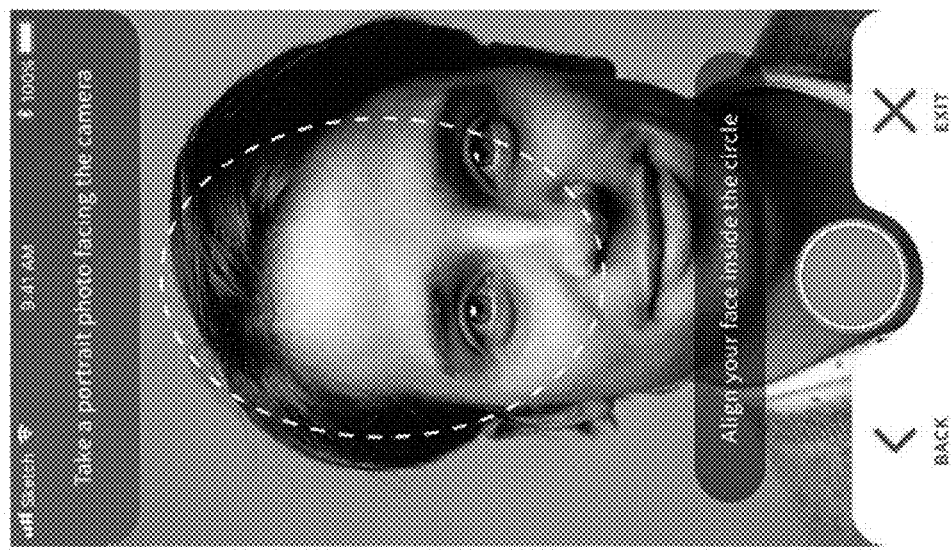
FIGS. 10A-10O illustrate an example of a computer device application, including possible steps taken by the user to submit data.
Figure 10H:
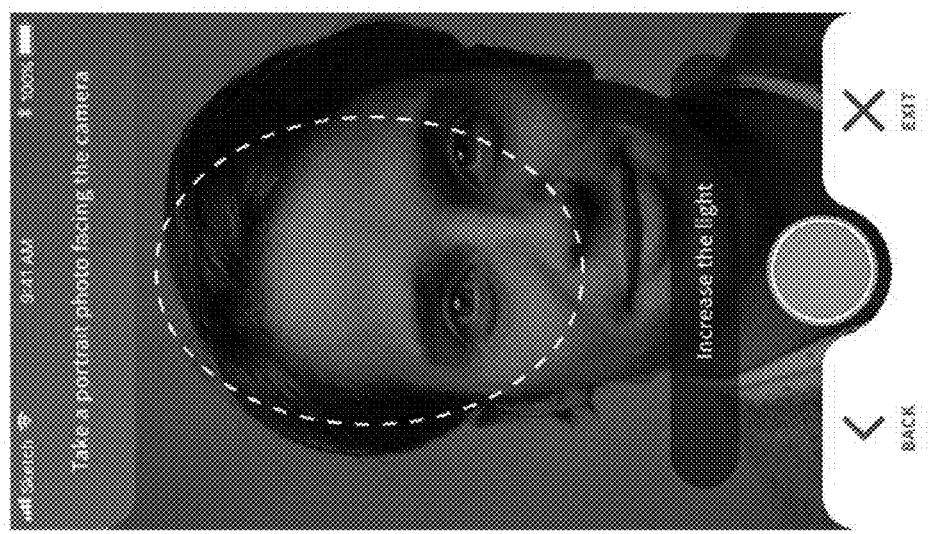
Figure 10G:
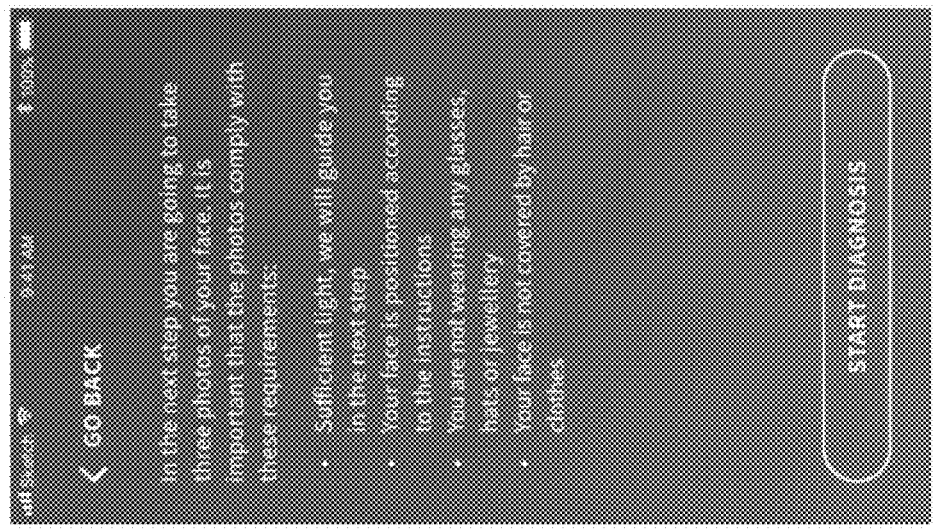
Figure 10L:
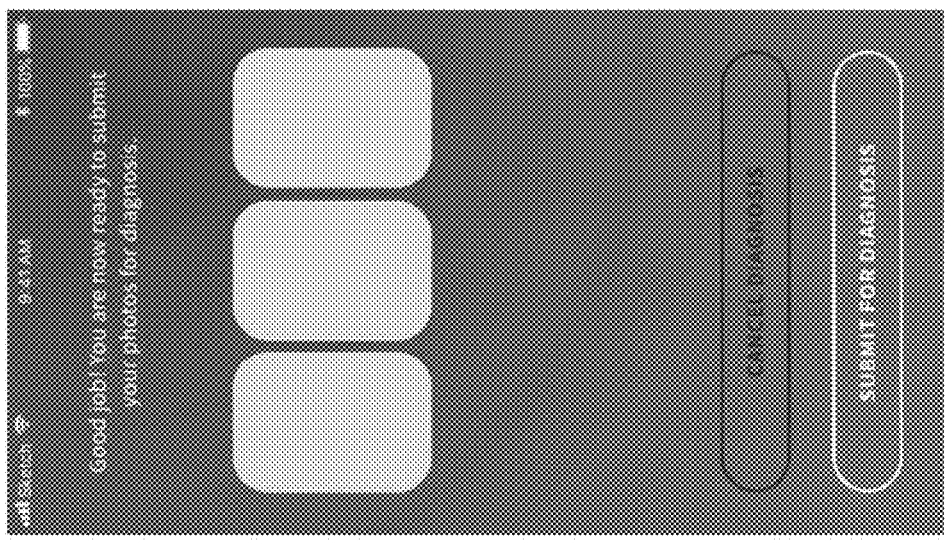
Figure 10K:
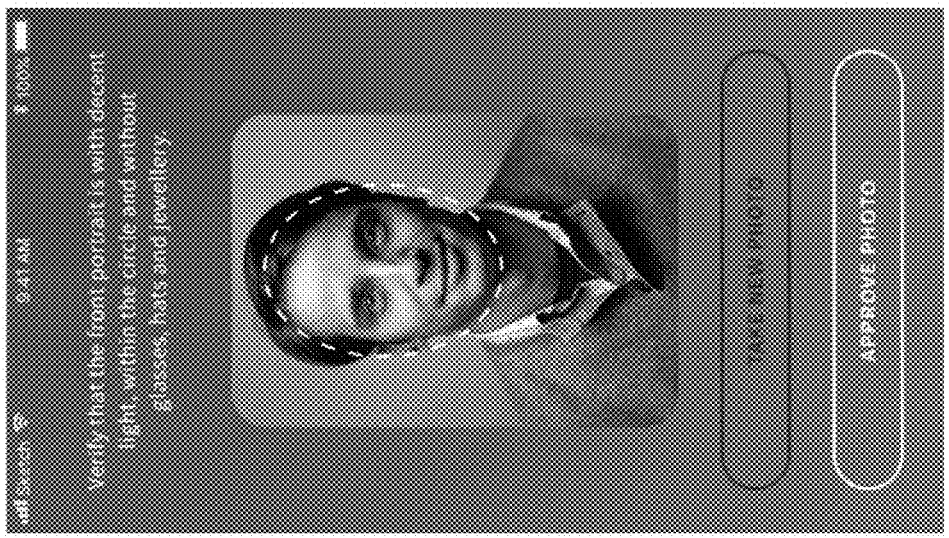
Figure 10J:
Figure 10O:
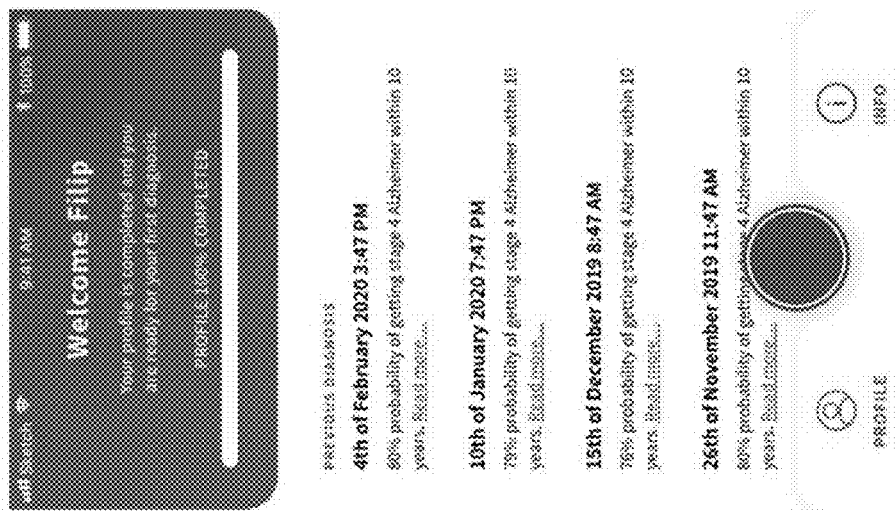
Figure 10N:
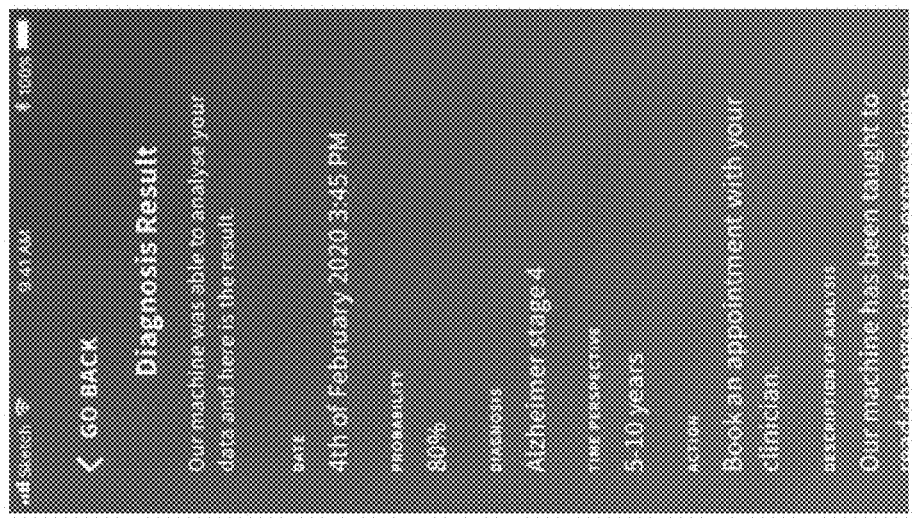
Figure 10M:
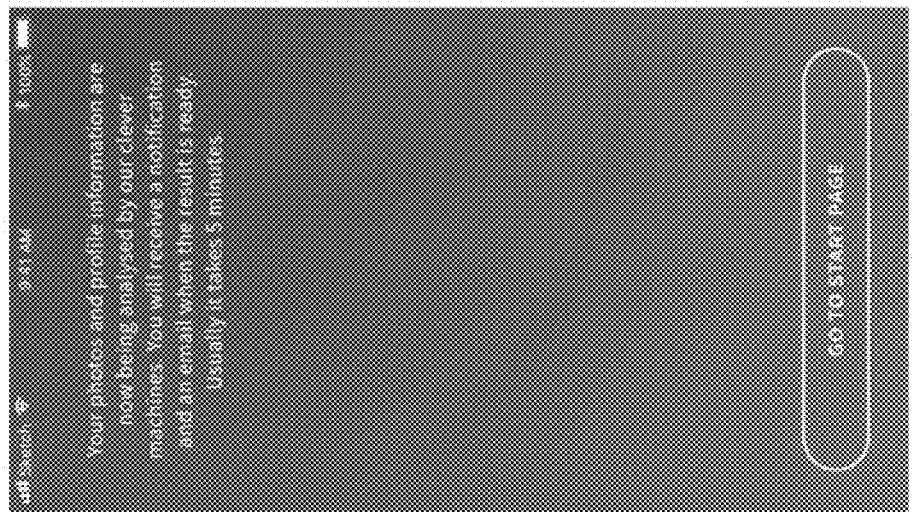

Data pertaining to the images, user-entered data as well as computer device data, may be transmitted to a server 24 over a network. The network may be a wired or a wireless network, and the examples may include but are not limited to the Internet, Wireless Local Area Network (WLAN), Wi-Fi, Long Term Evolution (LTE), Worldwide Interoperability for Microwave Access (WiMAX), and General Packet Radio Service (GPRS). FIGS. 10A—FIG. 10O illustrate what this process might look like when implemented on a computer device. Upon data transmission, datasets are generated 25, and machine learning analysis is performed on the datasets 26. The results of the machine learning analysis are then communicated to a specified party 27.

Figure 3A:
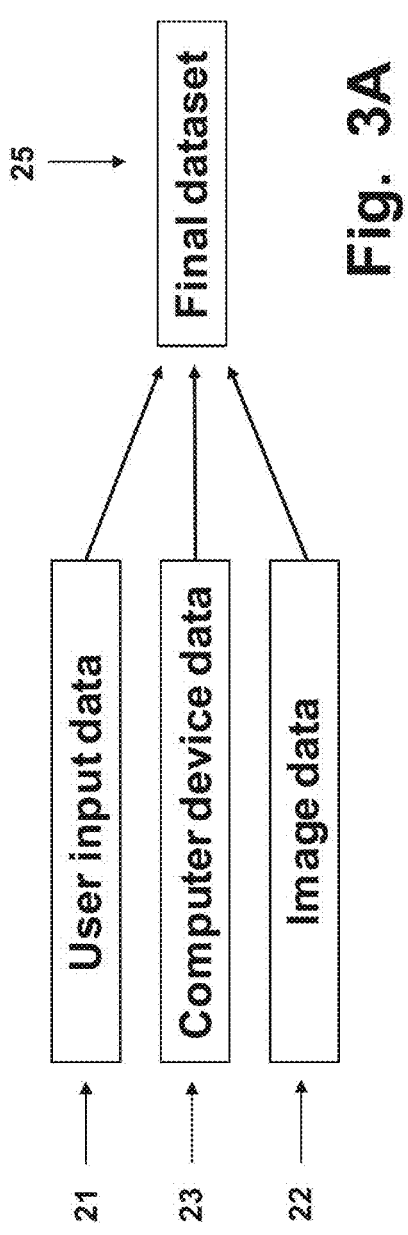
FIG. 3A and FIG. 3B illustrate an exemplary dataset generation process.

FIG. 3A illustrates the dataset generation process and based on the transmitted data from the previous step, one or more datasets are generated 25. In some examples of the invention, datasets 25 may be a temporary dataset 30 which may be segmented based on characteristics such as demographic characteristics including but not limited to gender and age to further enhance accuracy 31. This can be observed in FIG. 3B.

Based on previously trained machine learning models, dementia progression may then be estimated using machine learning methods 26. The results of the analysis may, but are not required to be, sent to the user's device and/or to a recipient of the user's choice 27. In some examples of the invention, the results may include a visualization of the estimated internal properties of the user's brain. It may furthermore also include a visualization of which parts of the head are most important in estimating the final results.

An overview of the machine learning process may be seen in FIG. 4. Like many machine learning processes, this method may follow steps of pre-processing the dataset to ensure that it is standardized, feature generation to relate variables to one another, training models using a variety of different machine learning algorithms, and predicting an outcome using the testing dataset.

Figure 5:
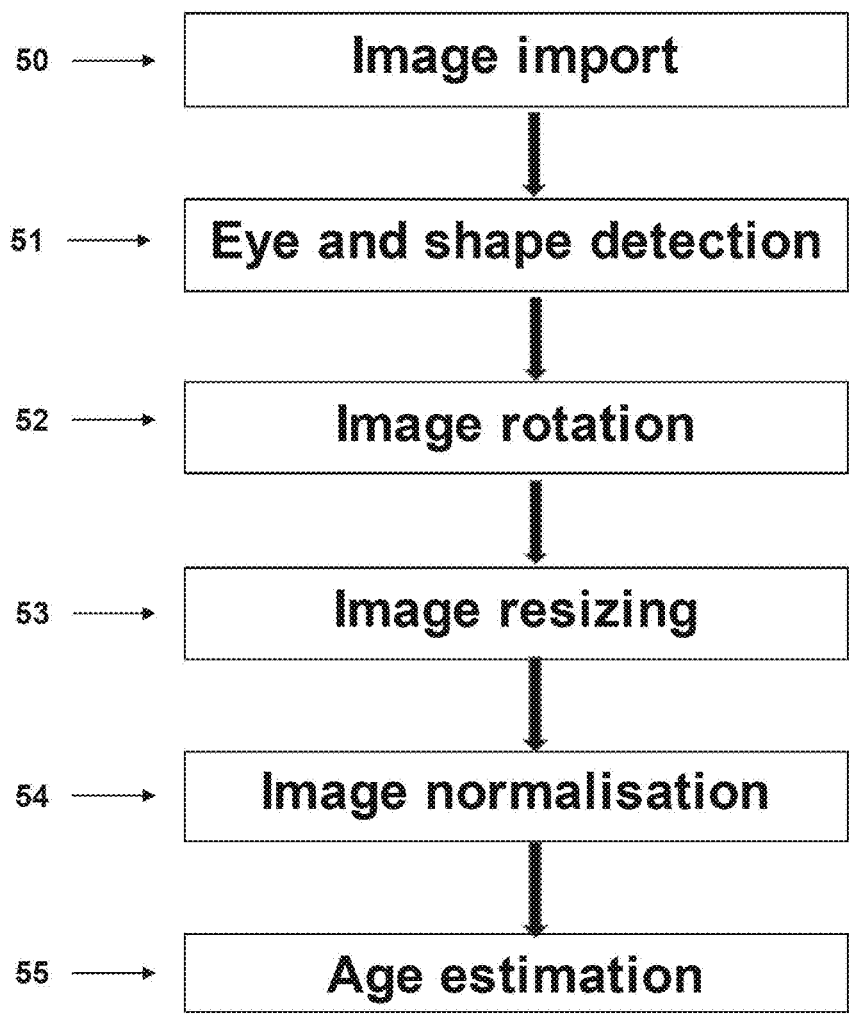
FIG. 5 illustrates an exemplary pre-processing part of a machine learning method that may be executed.

The machine learning part of the disclosure may take many forms. Like all machine learning problems, it is dependent on what the data looks like beforehand, and the most ideal machine learning method might change over time as new datasets become available. The generated dataset from dataset generation 25 step in FIG. 3A or the segmented dataset 31 in FIG. 3B, firstly goes through a preprocessing method 40. This includes importing image 50, normalizing, and resizing images to one standard 52, 53. Normalizing may in this embodiment take to mean any of but not limited to cropping, resizing, standardizing and ensuring comparability across data sources. Rotating images based on recognizing the eyes and shape of the head, and estimating the age of persons based on previously trained models. This preprocessing is illustrated in FIG. 5. Identifying the eyes and shape of a head 51 may be based on previously trained machine learning models, from a dataset of persons not related to the AD and dementia dataset. The image data may also be normalized 54 to change the data values to a common scale without distorting differences in the range of values to allow for a more robust machine learning process to be made. The age estimation procedure 55 may also be done through a previously trained machine learning model based on a dataset of persons not related to the AD and dementia dataset. Age estimation machine learning models are commonly used in the machine learning literature and several are publicly available for general use. Training an age estimation model entails using the age of the person in the image, identifying features and then training machine learning models to accurately predict the age of that person. The identified features will vary depending on the choice of machine learning methods as well as the types of persons included in sample and may look at features associated with wrinkles, gaze, skin colour, etc. The machine learning process may be executed in any general-purpose programming language such as but not limited to, Python, C++, JavaScript, Java, C#, Julia, Shell, R, TypeScript, and Scala.

Figure 6:
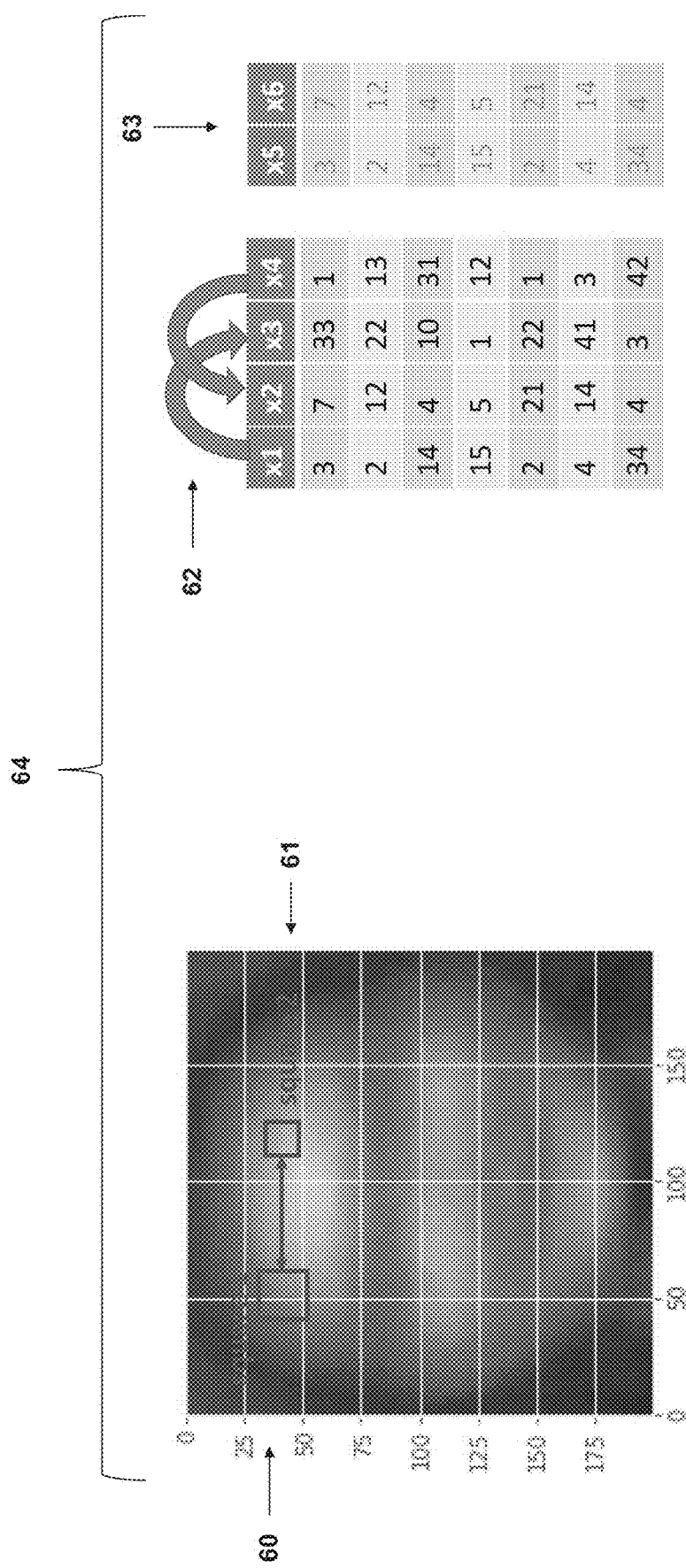
FIG. 6A and FIG. 6B illustrate an exemplary feature generation part of one machine learning process may work.

The feature generation step is illustrated in FIG. 6A and FIG. 6B. The feature generation step begins with randomly selecting an area of pixels from the image in question 60, and relating it to another randomly selected area of pixels 61. FIG. 6A is an example of this process where the [Max, min, median, mean and standard deviation] pixel values of the area represented by square 1 are divided by the same summary statistics in square 2 to create new variables. This seeks to measure the difference between different parts of the image and may provide meaningful information about small deviations, undetectable through more broad-based machine learning methods as well as the human eye, in the dataset. This same process is repeated on a number of different randomly chosen areas of the image. FIG. 6B represents this process in data-form, where each value represents a pixel value, and each column, and/or subsets of each column, can be related to one another 62 to create a larger dataset. After one iteration of this process, one might end up with one or more new columns such as x5, and x6 63 as additions to the database.

Figure 7:
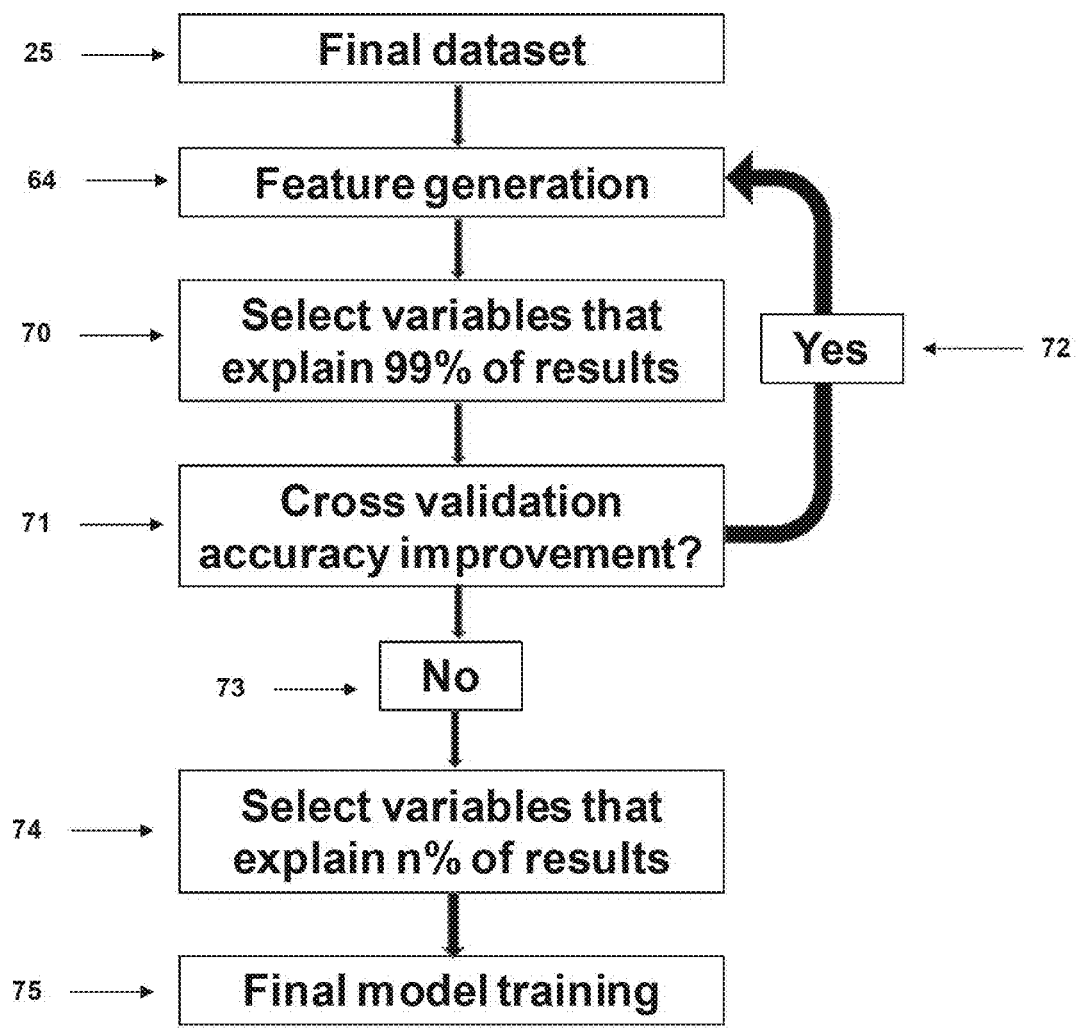
FIG. 7 illustrates an exemplary reiterative feature generation process that may be used in one or more machine learning processes.

The reiterative feature generation process develops this principle further and is illustrated in FIG. 7. In this instance, the generated dataset from dataset generation 25 step in FIG. 3A will be processed.

Figure 3B:
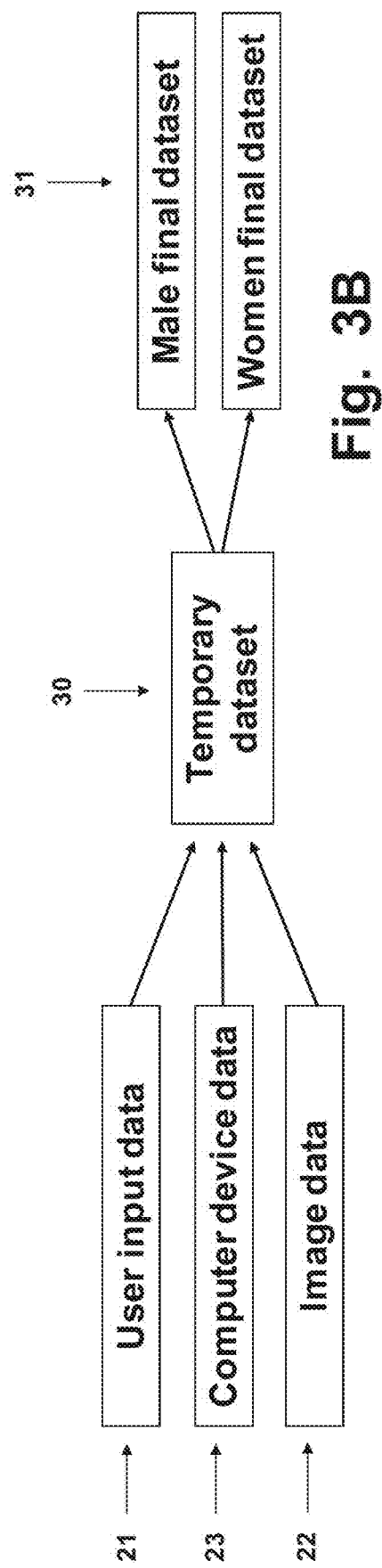

Alternatively, the generated dataset to be processed may be the segmented dataset 31 in FIG. 3B. The process may include random division, addition, and other data transformations between different variables in the generated dataset to ensure that variables keep being generated 64 until cross-validation shows no improvement 71, 72 to accuracies using a simple Random Forest Classification model. Cross-validation is in this instance taken to represent any model validation technique for assessing how a model result might generalize in an independent dataset. To reduce the computational challenges of including too many variables, after each feature generation process 64, the variables that explain 99% of the results are chosen 70, and the remaining variables are removed. Since many variables will be highly correlated, one can substantially speed up computational performance without losing important relationships. The next step in the process may be to check whether cross-validation accuracy has improved 71. If Yes 72, then the feature generation process 64 and variable selection step 70 will be repeated until cross-validation accuracy can no longer be improved 73. At this point, still using a standard Random Forest Classifier, the most important variables explaining n % of results 74 (as an example 30% may be an appropriate number), may be selected. The choice of n is in many cases arbitrary and might not affect the outcome to a large extent. What may be important, and standard machine learning practice is to have a well-balanced dataset. In this instance, it might mean that there shouldn't be too many variables for a set number of samples. With the remaining variables, the final predictive model may be trained 75.

The machine learning part of the disclosure may furthermore involve a cross-validation GridSearch using a number of machine learning algorithms. The choice of machine learning algorithms may include, but is not limited to, Logistic Regression, Naive Bayes, Nearest Neighbor, Support Vector Machines, Decision Trees, Boosted Trees, Random Forests, Neural Networks. It is not uncommon to have 2000+ models trained for each machine learning algorithm type in this step. The last machine learning step 75 may involve selecting the top models from the top n performing algorithm types, based on cross-validation scores, and then taking the mean probability of predictions to give a final prediction. Averaging predictions from several trained models may lead to more robust predictions in the out-of-sample testing data.

Figure 9:
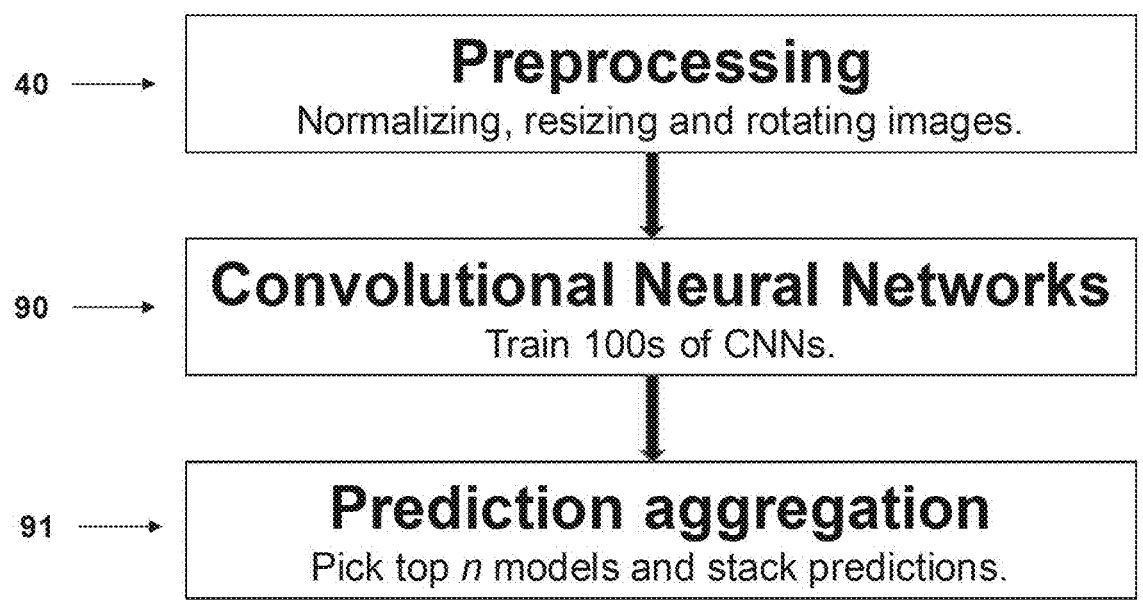
FIG. 9 illustrates an example of another machine learning method employing convolutional neural networks that may be used.

In another example of the disclosure, another machine learning process can be applied, as described in FIG. 9. In this example, the same pre-processing methods 40 described in previous steps are used, but instead of the feature generation processes and applying a number of different algorithms, only convolutional neural networks 90 are applied. Convolutional neural networks are a common machine learning method for image analysis and have been demonstrated to work particularly well on larger sample sizes. Several hundred such models are trained, and in accordance with the previously disclosed machine learning method, predictions from several of the trained models are averaged and aggregated to yield a final, more robust prediction on the out of sample dataset 91.

Resampling is a common method to adjust unbalanced datasets, for example where there may be one class that is more prevalent than another. Such resampling may help increase overall accuracy by making it easier for machine learning algorithms to learn on a synthetically balanced dataset instead. In some experiments, where either false positives or false negatives are considered particularly unwanted, such results in the dataset might be duplicated to increase their importance for the machine learning algorithms to learn more from these instances than others.

What has been described herein may in some examples be combined with a Cognitive Assessment tool. The Cognitive Assessment tool may be a questioner or an assessment to test the reaction of a subject. The cognitive assessment tool may also be a test to assess the memory of a subject. Other assessments may be spatial awareness or assessing a subject's ability to follow a straight line with a pen. The combination of the invention with Cognitive Assessment tools may help us further understand the progression of dementia and AD and may further our understanding of the complex interplay between visible manifestations of AD through physical changes to the brain, and cognitive symptoms that can be measured through Cognitive Assessment tools.

These cognitive assessment tools may be used to identify subjects who may need additional evaluation. None of the described tools are considered as the best brief assessment to determine if a full dementia evaluation may be needed. Several instruments have been identified as suited for use in primary care based on the following: administration time 5 minutes, validation in a primary care or community setting, psychometric equivalence or superiority to the Mini-Mental State Exam (MMSE), easy administration by non-physician staff and relatively free of educational, language and/or cultural bias. For a definitive diagnosis of mild cognitive impairment or dementia, individuals who fail any of these tests should be evaluated further or referred to a specialist.

Examples of Patient assessment tools that may be used to analyze the cognitive ability of a subject may be, General Practitioner Assessment of Cognition (GPCOG); Mini-Cog™; or Memory Impairment Screen. Examples of Informant tools for family members and close friends and which may be used to analyze the cognitive ability of a subject may be, Eight-item Informant Interview to Differentiate Aging and Dementia (AD8), General Practitioner Assessment of Cognition (GPCOG), Short Informant Questionnaire on Cognitive Decline in the Elderly (IQCODE).

In an example, patient assessment tools may include questions pertaining to different symptoms of different types and stages of dementia to differentiate between dementia and non-dementia subjects and the progression of dementia. Examples of cognitive characteristics that may be indicative of dementia may be focused on aphasia, attention (which may be indicative of posterior cortical atrophy), spatial reasoning (posterior cortical atrophy), emotion (changes to the hippocampus), visualization (changes to the parietal lobe), motivation (changes to hippocampus), spatial memory (changes to the entorhinal cortex).

Examples of questions that the user may be asked to estimate risk and progression of dementia may comprise:
1. Do you often struggle to find the right words (e.g., when answering questions, describing events or people)? (Aphasia)
2. Is it getting more difficult for you to pay attention (e.g., during conversations, while watching TV, reading)? (Attention: Posterior cortical atrophy)
3. Are you finding it increasingly difficult to estimate distances and/or measurements? (Spatial reasoning: Posterior cortical atrophy)
4. Are you finding it increasingly difficult to feel excitement? Emotion (Hippocampus)
5. Are you easily able to visualize yourself in your current physical situation? (Visualization: Parietal lobe)
6. Do you feel less motivated to see friends and family than before? (Motivation: Hippocampus)
7. Are you easily able to recall where things are located in your kitchen? (Spatial memory: Entorhinal cortex)

Examples of questions that the user may be asked to demonstrate indications of other forms of neurodegenerative disease may comprise:
1. Have you experienced changes in the way that you walk? (Vascular dementia)
2. Have you recently experienced a fall? (Lewy body disease)
3. Do you frequently experience disrupted sleep patterns? (Lewy body disease)

The questions may furthermore be weighted according to importance using machine learning and/or statistical methods. Such methods may include Principal Component Analysis and/or a plurality of clustering methods including but not limited to Affinity Propagation, Agglomerative Clustering, BIRCH, DBSCAN, K-Means, Mini-Batch K-Means, Mean Shift, OPTICS, Spectral Clustering and/or Gaussian Mixture Model, in order to enable a reduced questionnaire with only the most informative questions being used. Each question item importance may further depend on individual user information, such as gender and/or age, where machine learning methods can be used to identify non-linear interactions between characteristics pertaining to the user.

In an example, data pertaining to the user's genome and or microbiome may be used to further segment the patient's risk and/or progression of dementia. It is well known that prevalence of dementia correlates with certain genes (e.g., APOE c4 gene) as well as microbial diversity.

In an example, an analysis of features of the user's face may be used to indicate prevalence of genetic makeup of that user, and by extension whether certain of these genetic indications may demonstrate an increased risk of dementia. Facial characteristics are associated with genetic makeup and can be used for genotyping. Knowledge of this genetic predisposition can help segment these users better and therefore more accurately predict progression of dementia.

In an example, patient assessment tools may include cognitive assessment tests that have been designed to avoid a learning bias for the user. Examples of such tests may include tests that measure a user's reaction function, by showing images and instructing the user to react to the images, wherein the images are chosen to trigger a reactive response in a plurality of areas of the brain that may be indicative of the progression of dementia.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As will be appreciated by one of the skills in the art, the present disclosure may be embodied as device, system, and method or computer program product. Accordingly, the present disclosure may take the form of an entirely hardware embodiment, a software embodiment, or an embodiment combining software and hardware aspects all generally referred to herein as a "circuit" or "module." Furthermore, the present invention may take the form of a computer program product on a computer-readable storage medium having computer-usable program code embodied in the medium. Any suitable computer-readable medium may be utilized including hard disks, CD-ROMs, optical storage devices, transmission media such as those supporting the Internet or an intranet, or magnetic storage devices.

The present disclosure has been described above with reference to specific examples. However, other embodiments than the above described are equally possible within the scope of the invention. Different method steps than those described above, performing the method by hardware or software, may be provided within the scope of the disclosure. The different features and steps of the disclosure may be combined in other combinations than those described.

The scope of the disclosure may only be limited by the appended patent claims. Although modifications and changes may be suggested by those skilled in the art, the inventors intend to embody within the patent warranted heron all changes and modifications as reasonably and properly come within the scope of their contribution to the art.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases.

What is claimed is:

1. A computer-implemented method for non-invasive estimation of dementia progression of a subject, said method comprising:
   obtaining a plurality of still images which includes at least said subject's head from at least one angle; and
   identifying, said subject's head in said plurality of still images;
   processing, by a computer device and/or a server, said plurality of still images by performing a plurality of pre-processing steps;
   generating, by said server and/or said computer device, at least one dataset based on external features of said subject's head from said plurality still images;
   analyzing, by a plurality of machine learning models configured within said server and/or said computer device, said at least one dataset for patterns related to dementia symptoms, wherein said at least one dataset is analysed using said plurality of machine learning models trained on datasets based on external features of at least heads of dementia-diagnosed subjects; and
   estimating, by said machine learning models, progress of said dementia symptoms of said subject based on said analysis.

2. The computer-implemented method of claim 1, wherein said plurality of pre-processing steps comprising:
   importing said plurality of still images;
   detecting eyes and shape of the head based on one or more previously trained machine learning models;
   rotating the image based on detection of the eyes and shape of the head to one standard;
   normalizing the image to said one standard.

3. The computer-implemented method of claim 1, comprising a step of communicating the progress estimated by the machine learning models to the subject.

4. The computer-implemented method of claim 1, comprising a step of displaying one or more variables that are determining the progress of the dementia symptoms.

5. The computer-implemented method of claim 1, comprising a step of checking whether an input of subject-related information has been correctly entered.

6. The computer-implemented method of claim 1, comprising a step of estimating the age of the subject based on a previously trained machine learning model.

7. The computer-implemented method of claim 1, comprising a step of generating a visualization of internal properties of the brain of the subject.

8. The computer-implemented method of claim 1, comprising a step of combining data of the subject obtained through an electroencephalography (EEG) device with the dataset of the image.

9. The computer-implemented method of claim 1, wherein said obtaining said plurality of still images comprises:
   capturing said plurality of still images.

10. The computer-implemented method of claim 9, wherein said plurality of still images is captured using a camera or a computer device with a camera, such as a mobile phone.

11. The computer-implemented method of claim 10, comprising a step of detecting, by a gyroscope and an accelerometer, orientation of said camera or said computer device.

12. The computer-implemented method of claim 9, comprising a step of detecting lighting quality conditions and image quality conditions before capturing said image plurality of still images and prompting said subject to adjust said lighting quality conditions and/or said image quality conditions.

13. The computer-implemented method of claim 1, wherein answers to a questionnaire from the subject are received.

14. The computer-implemented method of claim 1, wherein said images are analyzed for the presence of artefacts and objects in the image that may indicate an increased risk of dementia.

15. The computer-implemented method of claim 1, wherein a metadata of the images is analyzed for patterns indicative of dementia.

16. The computer-implemented method of claim 1, wherein a temporal analysis of the subject's head images is performed by comparing a plurality of areas of the subject's head based on a recent set of one or more images with a plurality of areas of the subject's face in an older set of one or more images, and analyzing differences between these sets to estimate dementia progression.

17. The computer-implemented method of claim 1, wherein an emotion recognition model is applied to each image and said images are analyzed for temporal patterns of emotional deficit that may indicate dementia progression.

* * * * *